(12) United States Patent
Dunn et al.

(10) Patent No.: US 6,180,665 B1
(45) Date of Patent: Jan. 30, 2001

(54) CRYSTALLINE POLYMORPHIC FORM OF (S,S,S)-N-(1-[2-CARBOXY-3 (N2-MESYLLYSLAMINO) PROPYL]-1- CYCLOPENTYLCARBONYL) TYROSINE

(75) Inventors: Peter James Dunn; Michael Leslie Hughes, both of Sandwich (GB)

(73) Assignee: Pfizer Inc., New York, NY (US)

(*) Notice: Under 35 U.S.C. 154(b), the term of this patent shall be extended for 0 days.

(21) Appl. No.: 08/648,001

(22) PCT Filed: Nov. 9, 1994

(86) PCT No.: PCT/EP94/03750

§ 371 Date: May 28, 1996

§ 102(e) Date: May 28, 1996

(87) PCT Pub. No.: WO95/15308

PCT Pub. Date: Jun. 8, 1995

(30) Foreign Application Priority Data

Dec. 4, 1993 (GB) .................................. 9324931

(51) Int. Cl.$^7$ .......................... C07C 37/10; C07C 41/10; C07C 317/06

(52) U.S. Cl. .......................... 514/533; 514/562; 560/13; 562/430

(58) Field of Search .............................. 560/13; 562/430; 514/533, 562

(56) References Cited

FOREIGN PATENT DOCUMENTS 0358398 3/1990 (EP) .
9406756 3/1994 (WO) .

OTHER PUBLICATIONS

Protective Groups in Organic Synthesis, 2nd ed., Green and Wuts, John Willey and Sons, Inc., NY, 1991.*

* cited by examiner

Primary Examiner—Deborah Carr
Assistant Examiner—Brian J. Davis
(74) Attorney, Agent, or Firm—Peter C. Richardson; Gregg. C. Benson; A. Dean Olson

(57) ABSTRACT

The present invention relates to a crystalline, α-polymorphic form of a compound of formula (I) and to processes for the preparation of, to intermediates used in the preparation of, to compositions containing and to uses of, the α-polymorphic form.

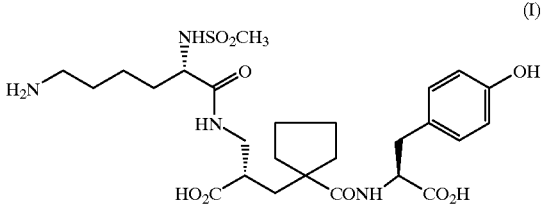

(I)

18 Claims, 21 Drawing Sheets

IR spectrum of the α-form as a nujol mull on a sodium chloride disc with air as the reference
(ν = 4000–400 cm⁻¹)

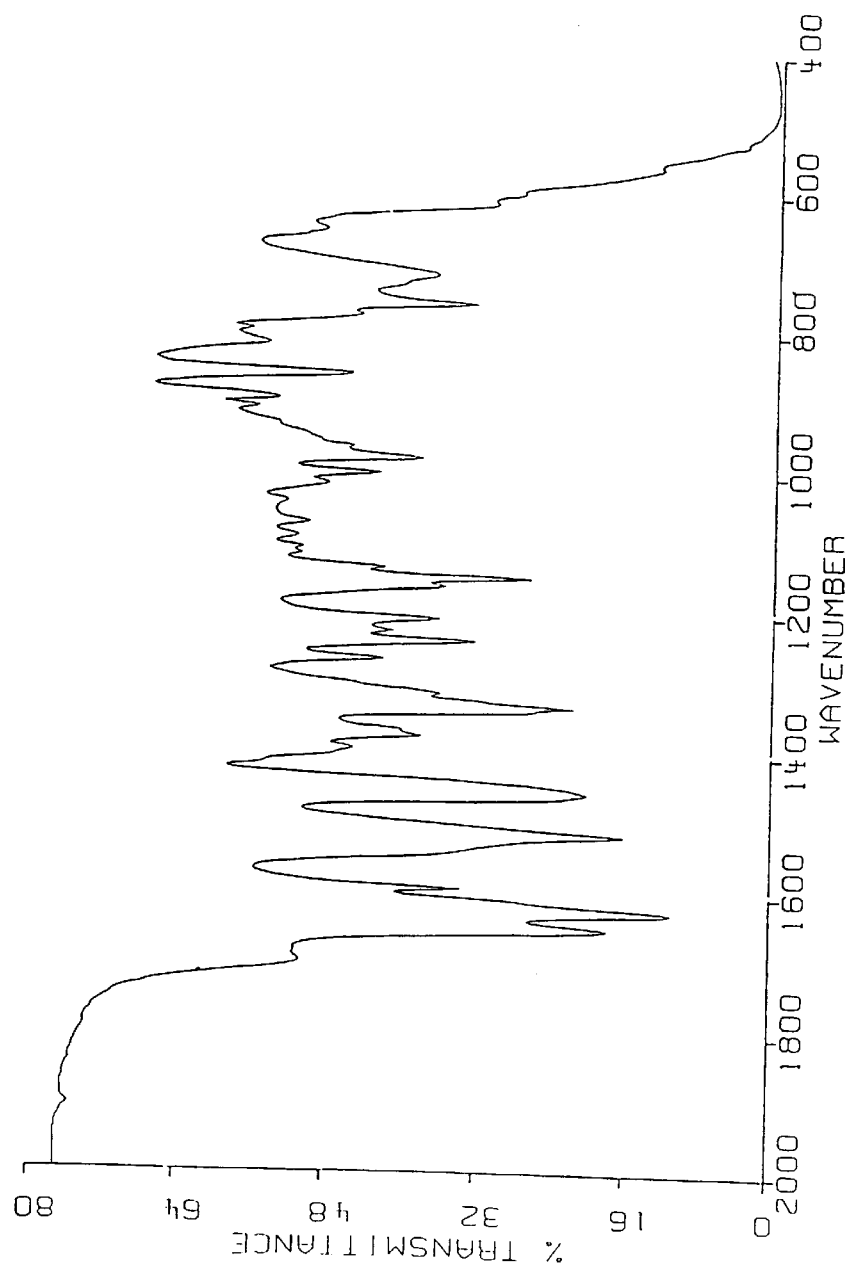

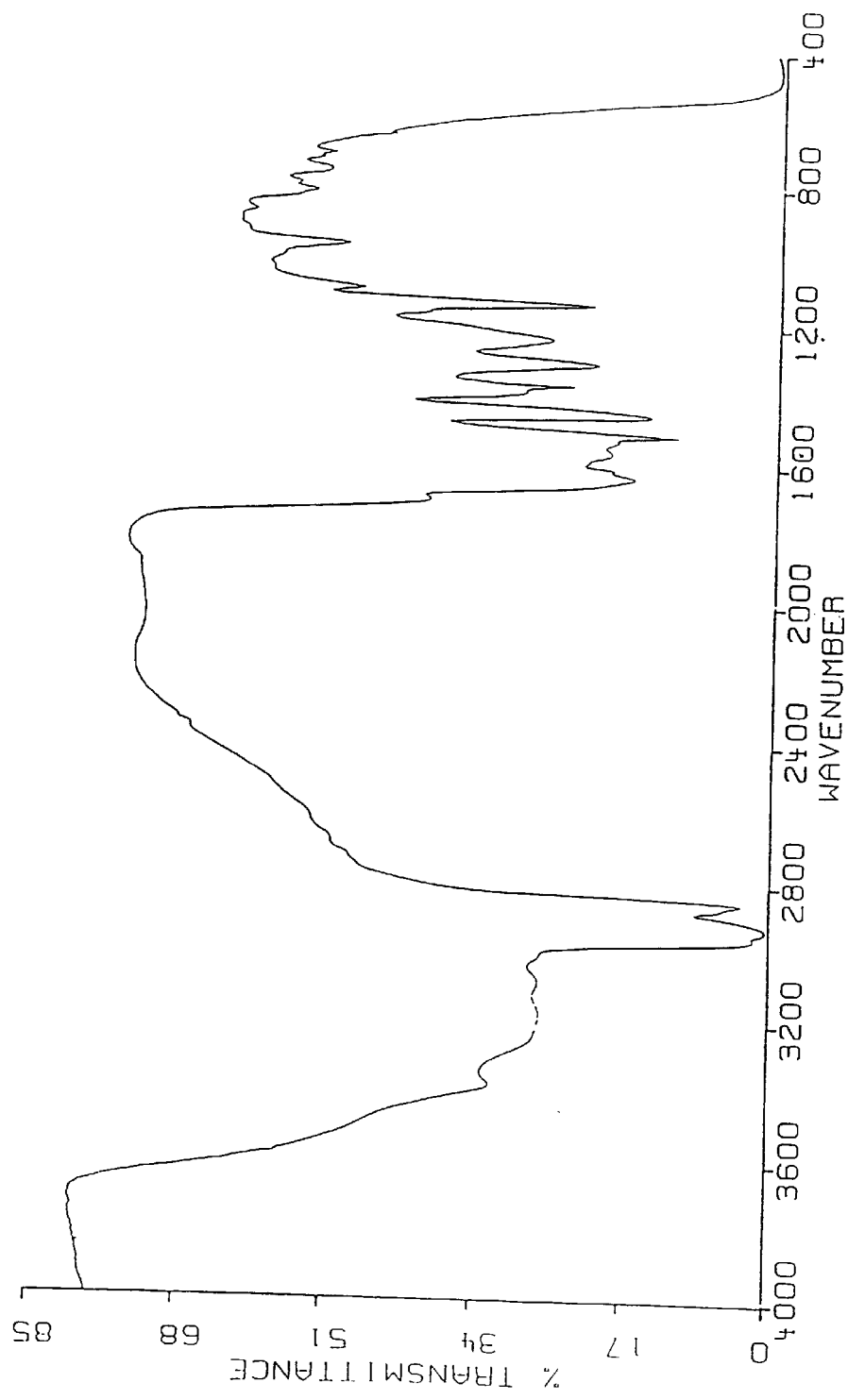

IR spectrum of the ß-form as a nujol mull on a sodium chloride disc with air as the reference
($\nu = 2000-400 cm^{-1}$)

IR spectrum of the γ-form as a nujol mull on a sodium chloride disc with air as the reference
($\nu = 4000–400 cm^{-1}$)

IR spectrum of the γ-form as a nujol mull on a sodium chloride disc with air as the reference
($\nu = 2000\text{-}400 \text{cm}^{-1}$)

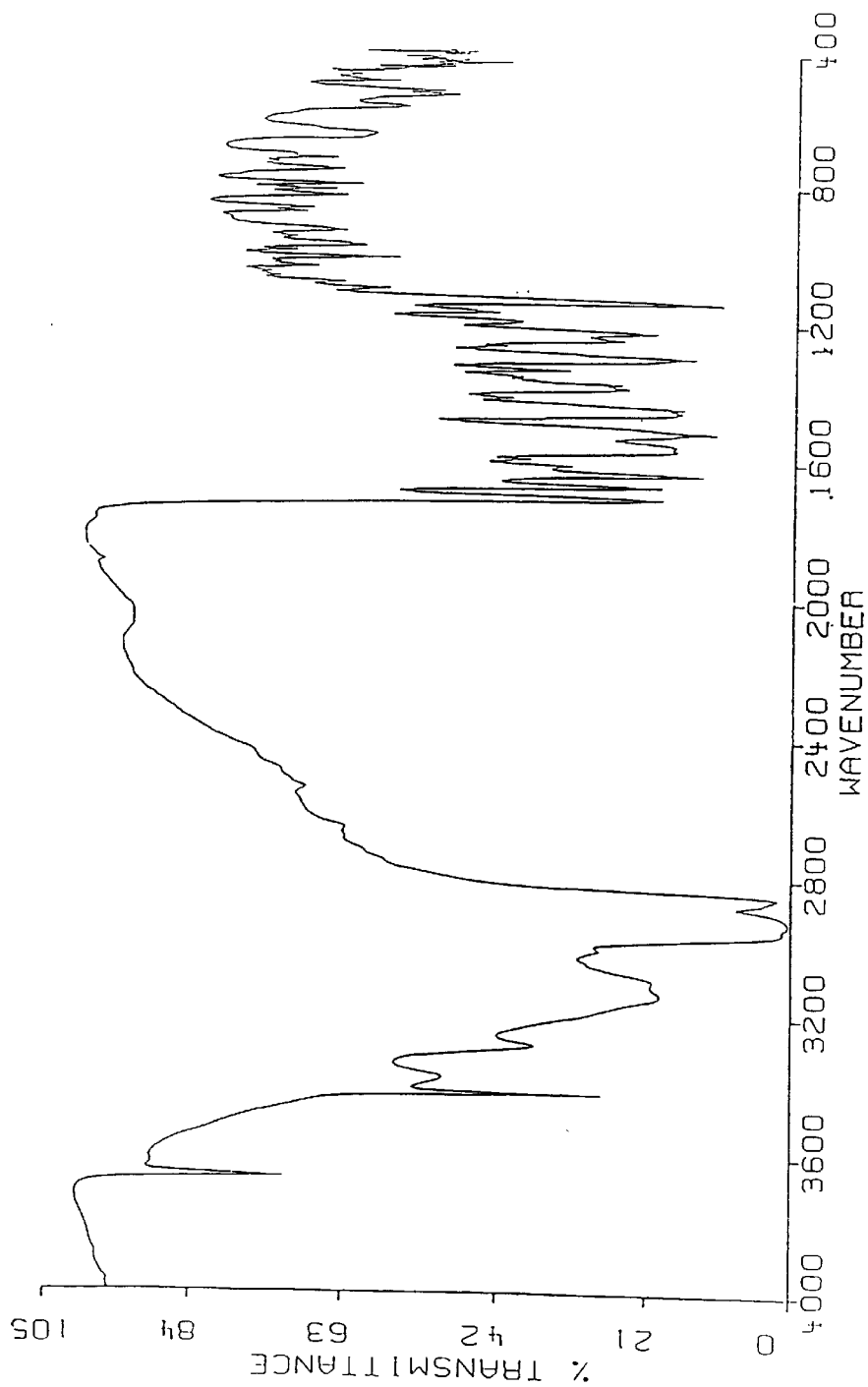

IR spectrum of the δ-form as a nujol mull on a sodium chloride disc with a nujol on sodium chloride disc reference ($\nu = 2000-400 cm^{-1}$)

PXRD of the α-form

PXRD of the ß-form

PXRD of the γ-form

PXRD of the δ-form

DSC thermogram of the α-form

DSC thermogram of ß-form

DSC thermogram of γ-form

Graph plotting upper punch force as a function of number of tablets for an Avicel/DCP placebo blend Graph plotting ejection force (kN) as a function of number of tablets for the α- and β-form blends Graph plotting mean percentage change in weight as a function of time for the α- and β-forms at 40°C and at various relative humidities (RH)

Moisture sorption of the α- and ß-forms at 40°C with exposure to increasing relative humidities

CRYSTALLINE POLYMORPHIC FORM OF (S,S,S)-N-(1-[2-CARBOXY-3 (N2-MESYLLYSLAMINO) PROPYL]-1- CYCLOPENTYLCARBONYL) TYROSINE

This application was filed under 35 U.S.C. §371 based on PCT/EP94/03750, which was filed on Nov. 9, 1994 which claims priority from U.K. application serial no. 9324931.6 which was filed on Dec. 4, 1993 and is now abandoned.

The present invention relates to a crystalline, polymorphic form of (S,S,S)-N-(1-[2-carboxy-3-($N^2$-mesyllysylamino)propyl]-1-cyclopentylcarbonyl)tyrosine which has the formula:

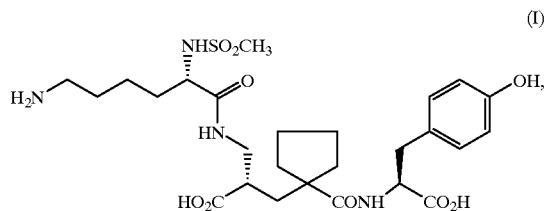

hereafter referred to as the "α-form" of a compound of the formula (I).

More particularly, the invention relates to the α-form of a compound of the formula (I) and to processes for the preparation of, to intermediates used in the preparation of, to compositions containing and to uses of, the α-form.

An amorphous form (hereafter referred to as the "β-form") of a compound of the formula (I) has been disclosed in European Patent Publication No. EP-A-0358398 as Example 181. The compound is a potent inhibitor of the zinc dependent neutral endopeptidase E.C.3.4.24.11 and is therefore able to potentiate the biological effects of atrial natriuretic factor. It is therefore a natriuretic, antihypertensive and diuretic agent that is useful for the treatment of various cardiovascular disorders. The compound is also a potent inhibitor of angiotensin converting enzyme, a further enzyme that is involved in the control of blood pressure. The compound therefore has a dual pharmacological action through being capable of inhibiting two key enzymes involved in the control of blood pressure. It is therefore likely to be useful in the treatment of various forms of hypertension and associated cardiovascular disorders such as congestive heart failure and glaucoma.

The β-form can be obtained by methods such as freeze drying of a solution of the compound of the formula (I), by rapid evaporation of the solvent from such a solution or by precipitation from such a solution by addition of a poor solvent. The β-form does not melt sharply but normally "softens" at about 160° C.

The β-form has, however, been found to have certain properties which do not make it particularly suitable for pharmaceutical formulation. In particular it is hygroscopic in nature, it has a low bulk density and poor flow properties. Processing experiments carried out using the β-form have revealed problems in manufacturing tablets from compositions containing this form.

The problem addressed by the present invention is the provision of a form of the compound of the formula (I) which can be efficiently processed to provide a stable and effective formulation of the drug.

This problem has been solved by the surprising finding that an α-form of a compound of the formula (I) can be prepared which is non-hygroscopic, crystalline and, when compared to the β-form, which has a higher bulk density and better flow properties. The α-form is particularly suitable for use in pharmaceutical formulation of the drug.

The present invention therefore provides a crystalline, polymorphic α-form of a compound of the formula (I) which has an infra-red spectrum as a mull in nujol which shows absorption bands at ν=3407, 3386, 3223, 3153, 1699, 1652, 1626, 1594, 1516, 1457 (nujol), 1377 (nujol), 1344, 1334, 1317, 1267, 1241, 1228, 1210, 1164, 1151, 1137, 1118, 1109, 1093, 1074, 1045, 1019, 1003, 981, 965, 911, 897, 862, 818, 800, 778, 762, 721 and 655 $cm^{-1}$.

The α-form is further characterised by its powder X-ray diffraction pattern obtained using copper radiation filtered with a graphite monochromator (λ=0.15405 nm) which shows main peaks at 7.5, 8.9, 9.9, 11.6, 15.6, 17.2, 17.5, 18.0, 20.2, 22.1 and 23.3 degrees 2θ.

The α-form is yet further characterised by differential scanning calorimetry in which it shows a sharp endotherm in the range 248–259° C. and decomposes at above 260° C. when subjected to a scanning rate of 20° C. per minute.

The α-form typically melts sharply in the range 242–252° C., although lower melting point ranges have been recorded.

Other forms (hereafter referred to as the "γ-" and "δ-forms") of a compound of the formula (I) have also been obtained which also form part of the present invention since they can be used as intermediates in the preparation of the α-form.

The invention thus further provides a polymorphic γ-form of a compound of the formula (I) which has an infra-red spectrum as a mull in nujol which shows absorption bands at ν=3377, 3240, 1665, 1639, 1594, 1527, 1518, 1494, 1457 (nujol), 1443, 1377 (nujol), 1344, 1321, 1304, 1254, 1195, 1178, 1162, 1143, 1111, 1098, 1046, 1031, 1012, 972, 962, 945, 932, 907, 879, 849, 815, 806, 780, 753, 729 and 658 $cm^{-1}$.

The γ-form is further characterised by its powder X-ray diffraction pattern obtained using copper radiation filtered with a graphite monochromator (λ=0.15405 nm) which shows main peaks at 9.0, 9.6, 10.6, 11.6, 12.7, 13.3, 14.6, 16.2, 17.9, 18.8, 20.2 and 21.8 degrees 2θ.

The γ-form is yet further characterised by differential scanning calorimetry in which it shows a sharp endotherm in the range 176–186° C., an exotherm at about 207° C. and a weak endotherm at about 213° C. and decomposes at above 250° C. when subjected to a scanning rate of 20° C. per minute.

The γ-form typically melts sharply in the range 170–185° C.

The invention thus also provides a hydrated δ-form of a compound of the formula (I) which has a water content of from 1 to 7%, preferably of from 2 to 4%, by weight, as determined by Karl Fischer analysis, and which has an infra-red spectrum as a mull in nujol which shows absorption bands at ν=3667, 3425, 3380, 3287, 3137, 3098, 1709, 1673, 1637, 1619, 1596, 1568, 1556, 1516, 1458 (nujol), 1448, 1419, 1390, 1378 (nujol), 1356, 1338, 1300, 1270, 1249, 1229, 1198, 1174, 1141, 1108, 1091, 1075, 1064, 1045, 1033, 1019, 1001, 985, 962, 941, 909, 889, 877, 841, 822, 807, 763, 744, 732, 721 and 655 $cm^{-1}$ The δ-form is further characterised by its powder X-ray diffraction pattern obtained using copper radiation filtered with a graphite monochromator (λ=0.15405 nm) which shows main peaks at 10.5, 10.8, 12.3, 14.5, 17.2, 17.6, 17.9

The δ-form is yet further characterised by differential scanning calorimetry in which it shows sharp endotherms at about 162° C. and at about 166–168° C. and decomposes at above 200° C. when subjected to a scanning rate of 20° C. per minute.

The δ-form typically melts sharply in the range 165–175° C.

Although the γ- and δ-forms of a compound of the formula (I) display the same pharmacological activities as the α- and β-forms, they are not as suitable as the α-form for the purpose of pharmaceutical formulation.

BRIEF DESCRIPTION OF THE DRAWINGS

FIGS. 1A, 1B, 2A, 2B, 3A, 3B, 4A and 4B are IR spectra for certain polymorphs of (S,S,S)-N-(1-[2-carboxy-3-($N^2$-mesyllysylamino)propyl]-1-cyclopentylcarbonyl)tyrosine.

Figure 1A:
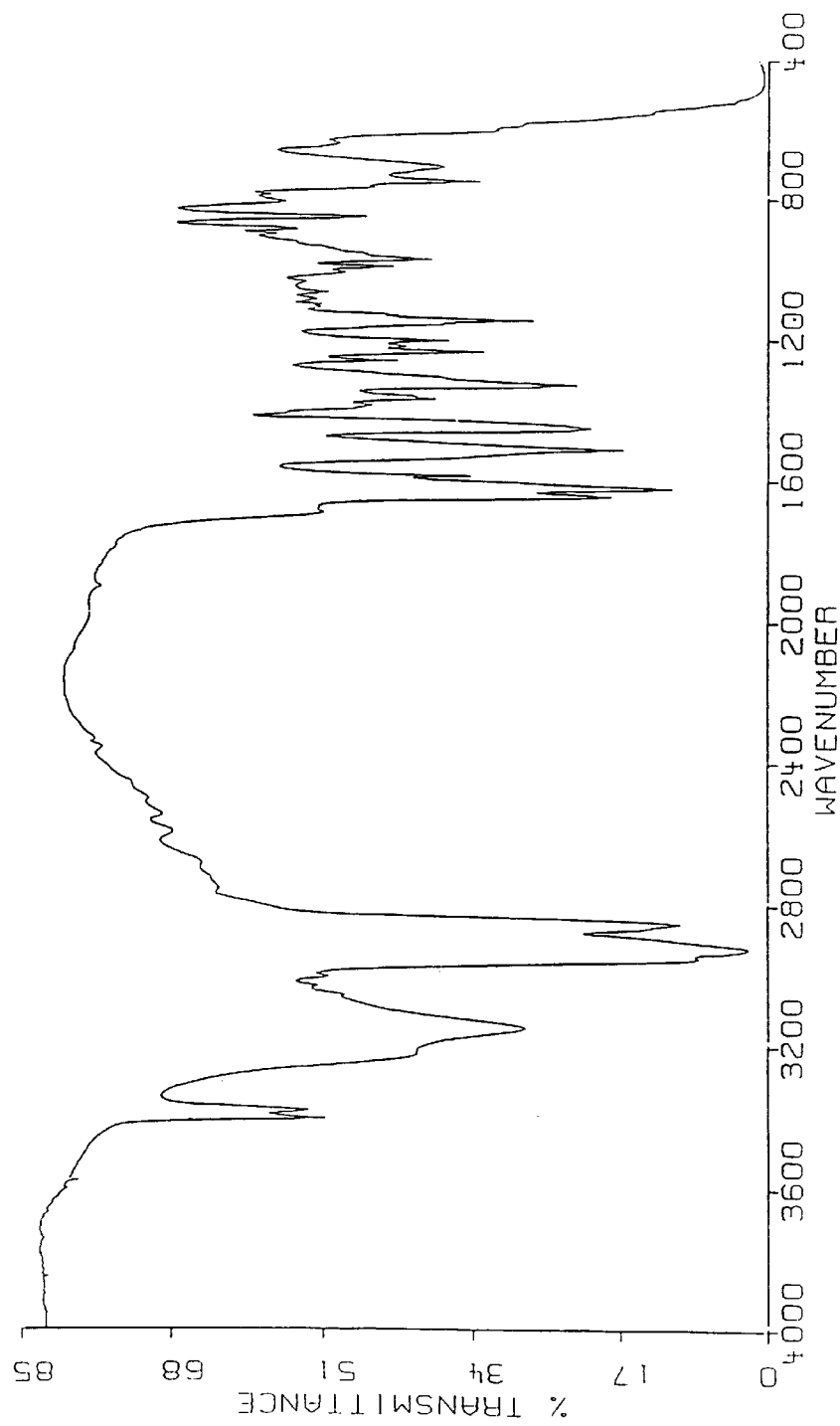
Figure 2B:
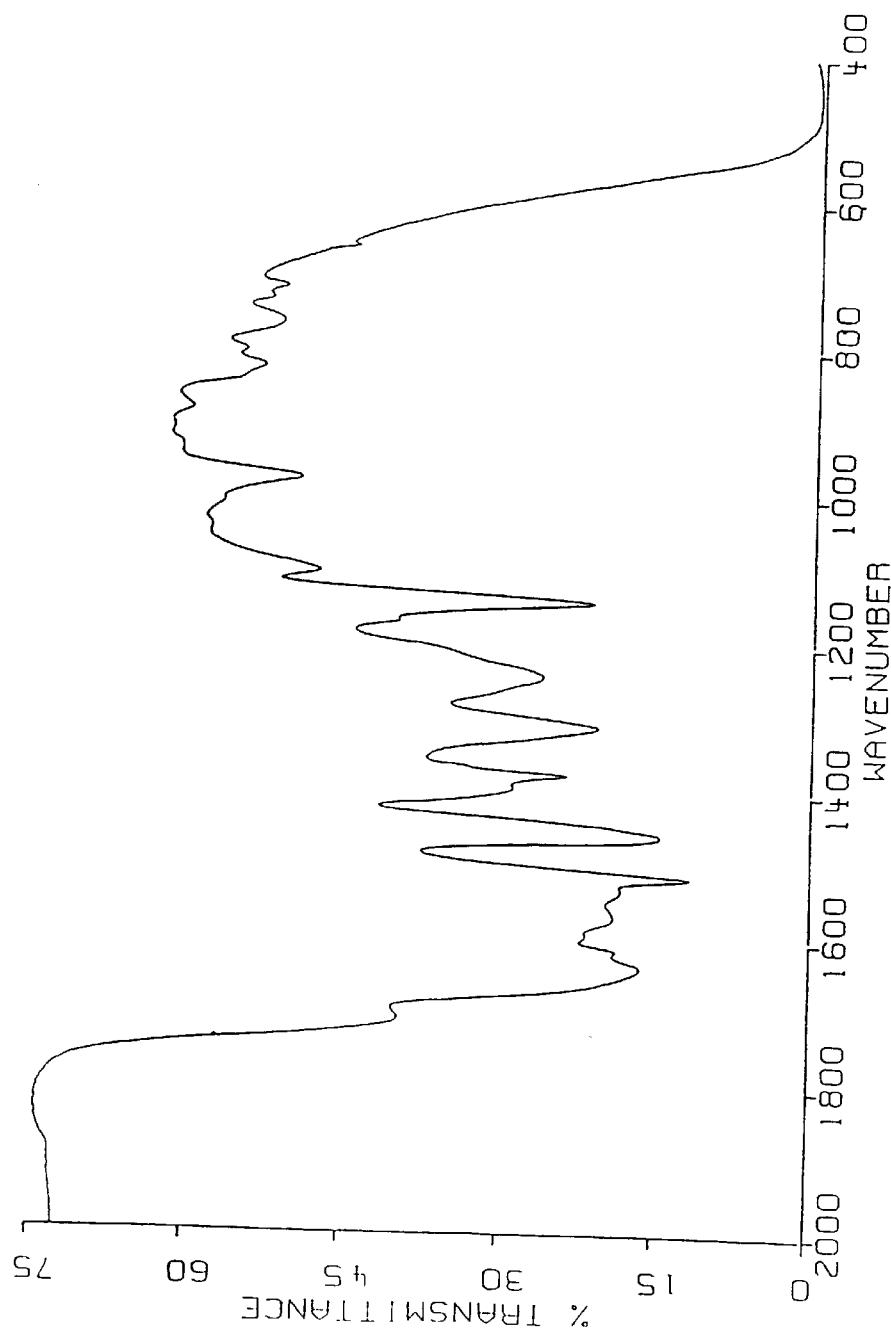
Figure 3A:
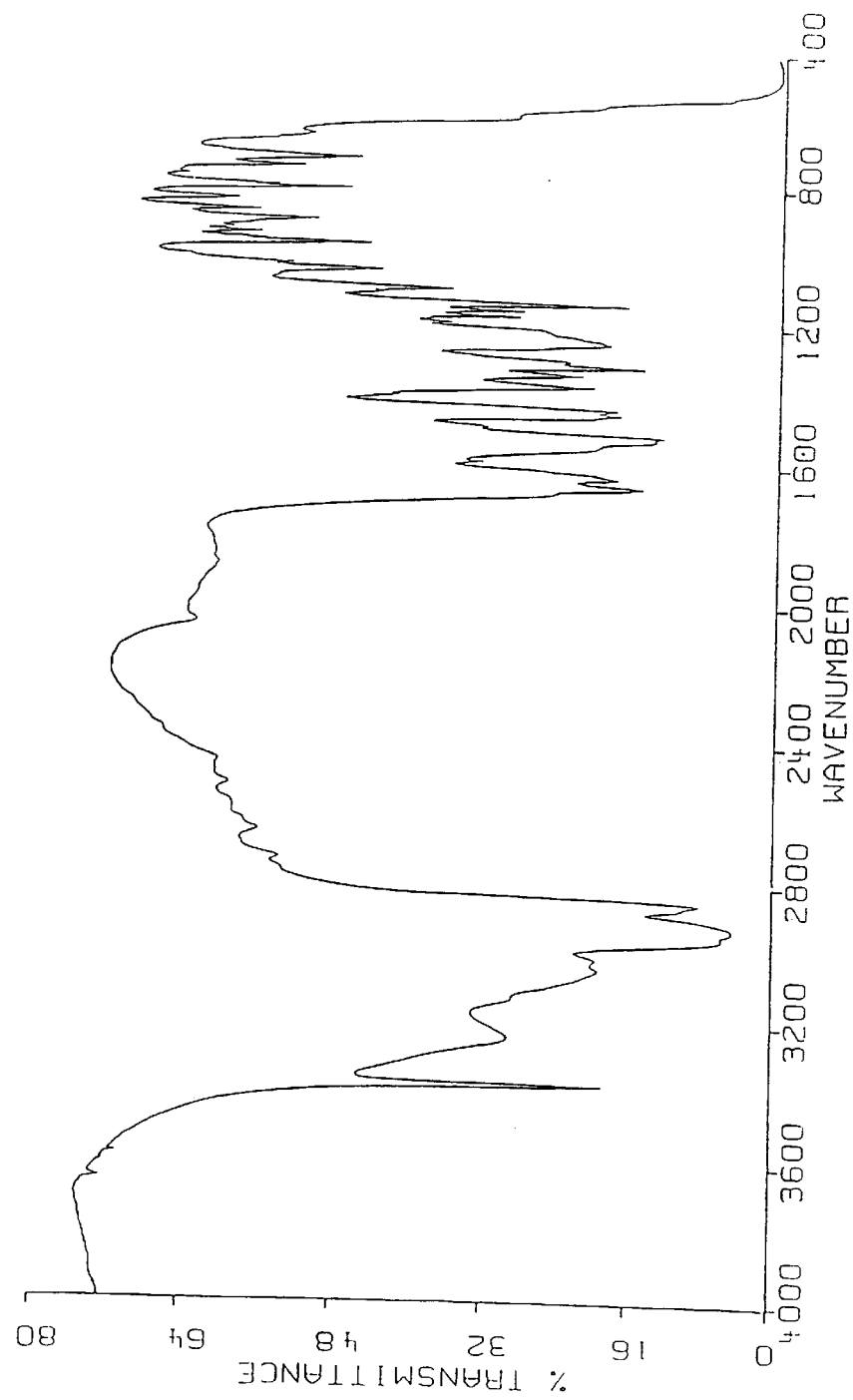
Figure 3B:
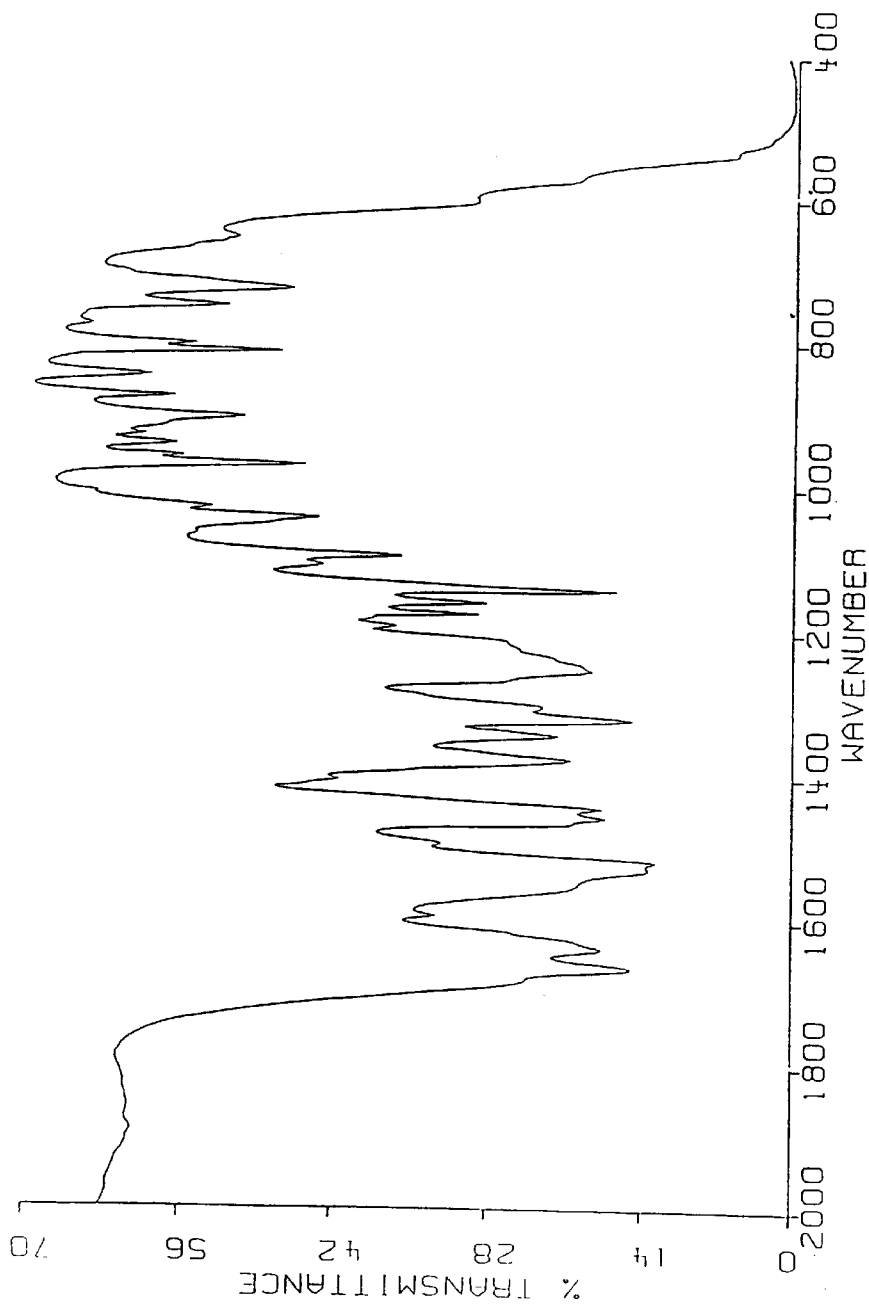
Figure 4B:
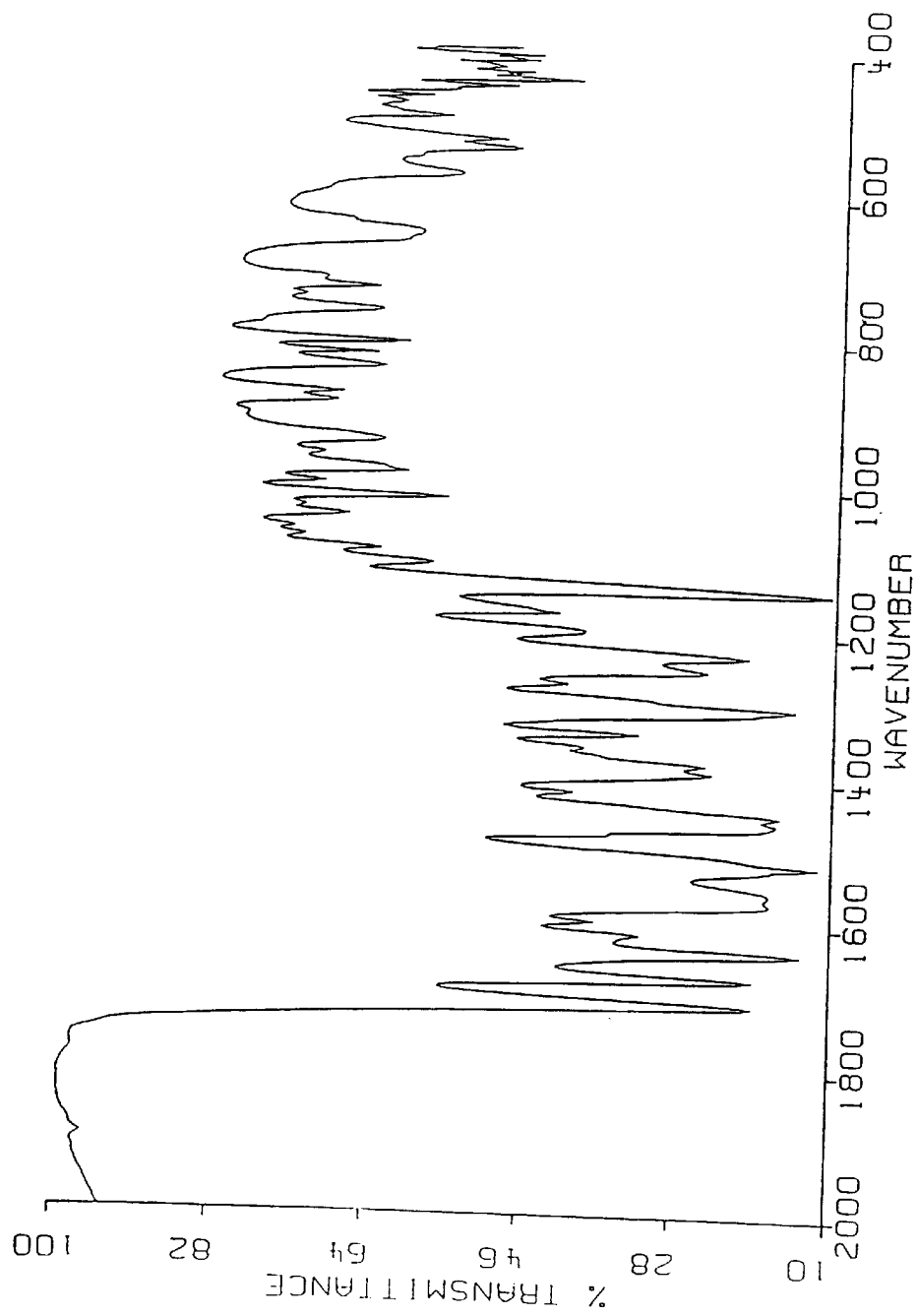
Figure 5:
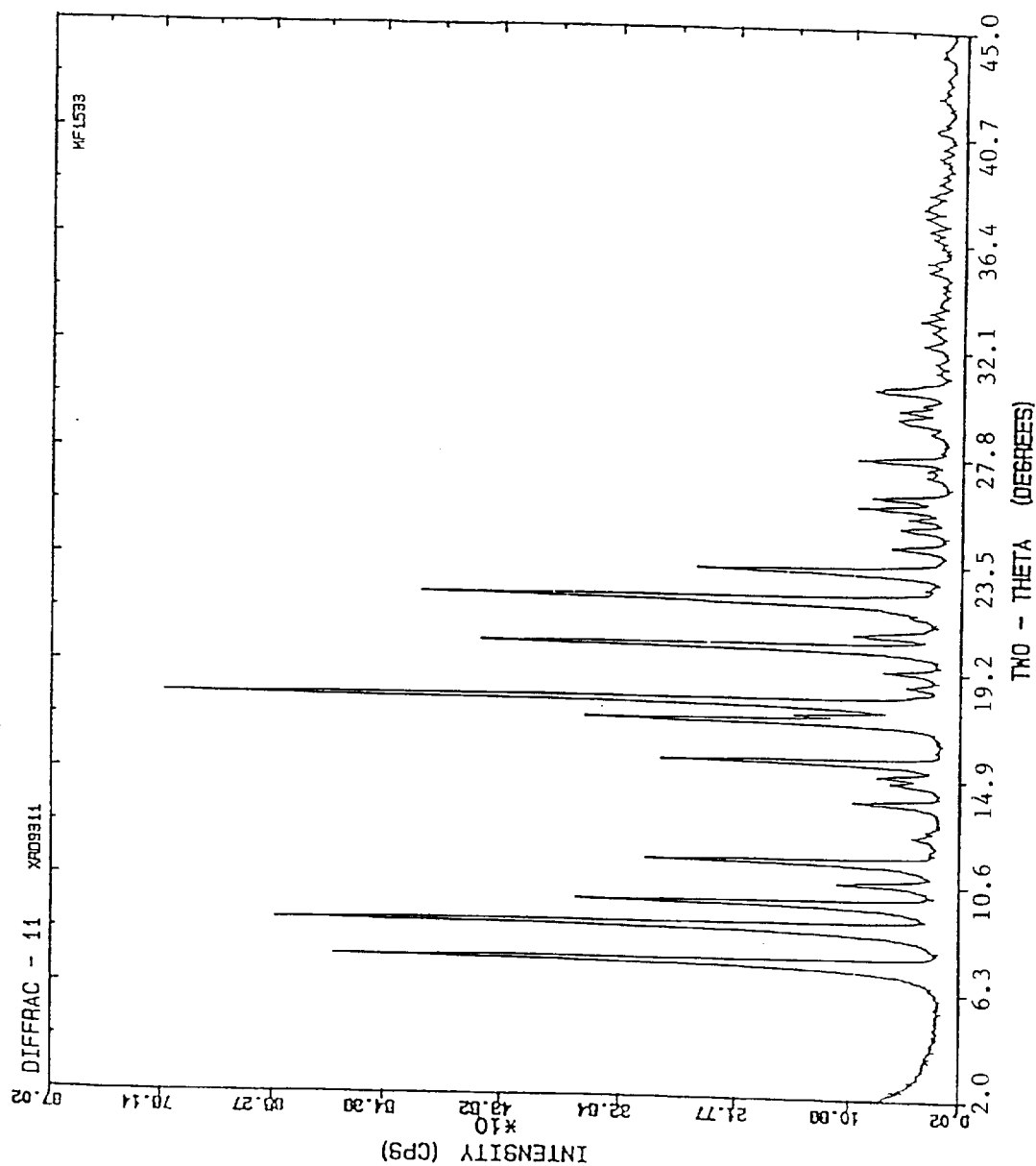
FIGS. 5–8 are PXRD patterns of certain polymorphs of (S,S,S)-N-(1-[2-carboxy-3-($N^2$-mesyllysylamino)propyl]-1-cyclopentylcarbonyl)tyrosine.
Figure 6:
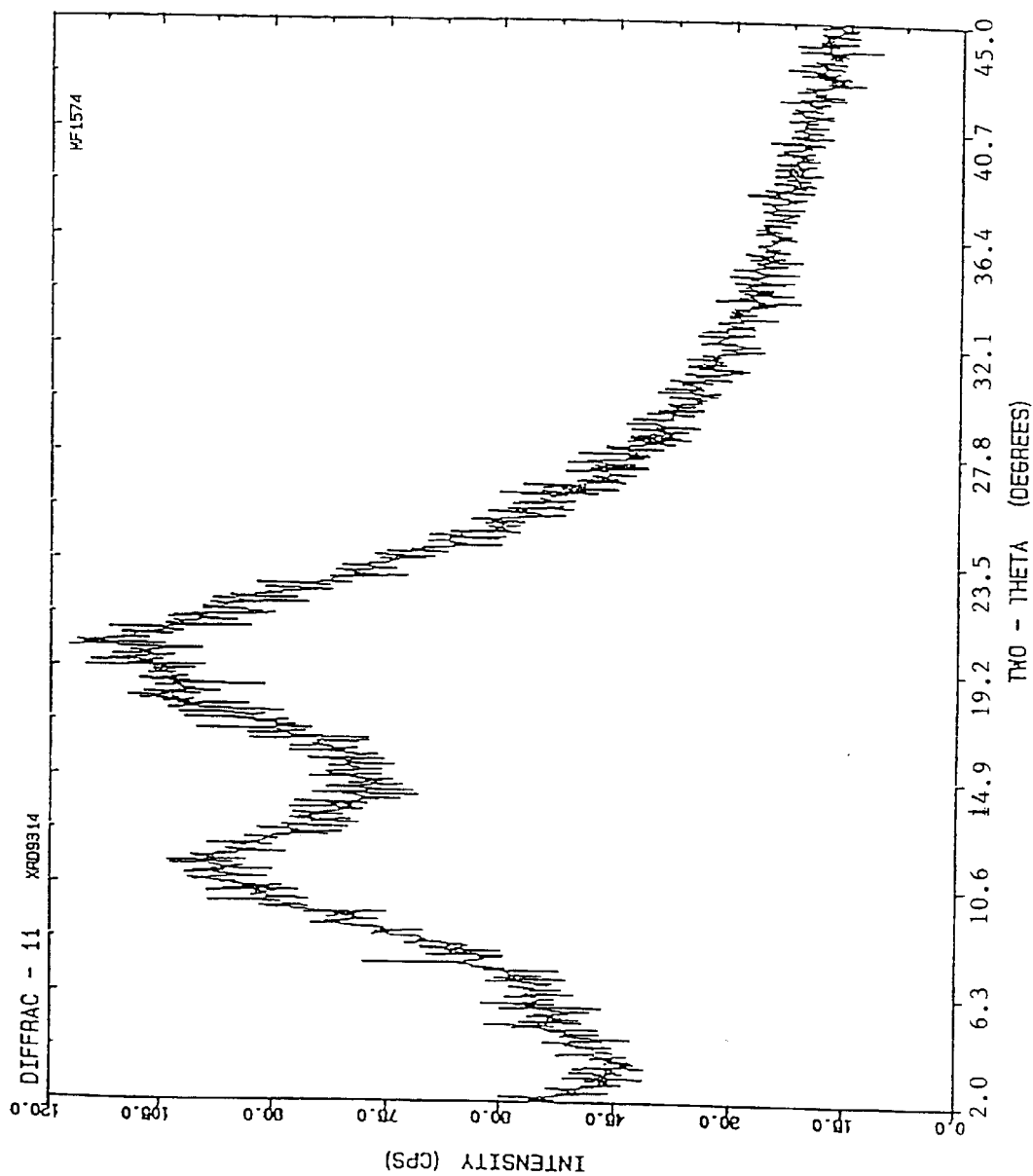
Figure 7:
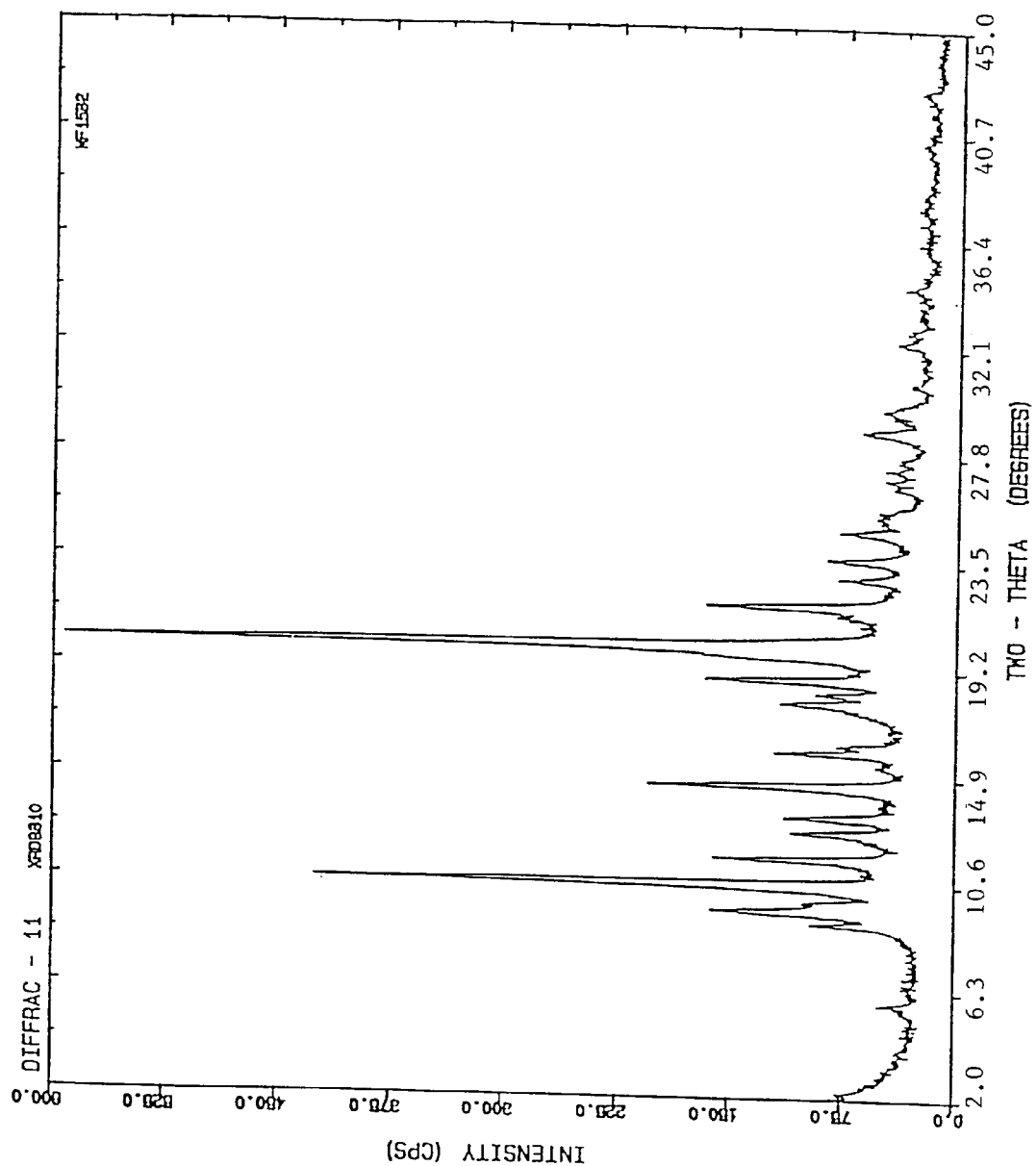
Figure 8:
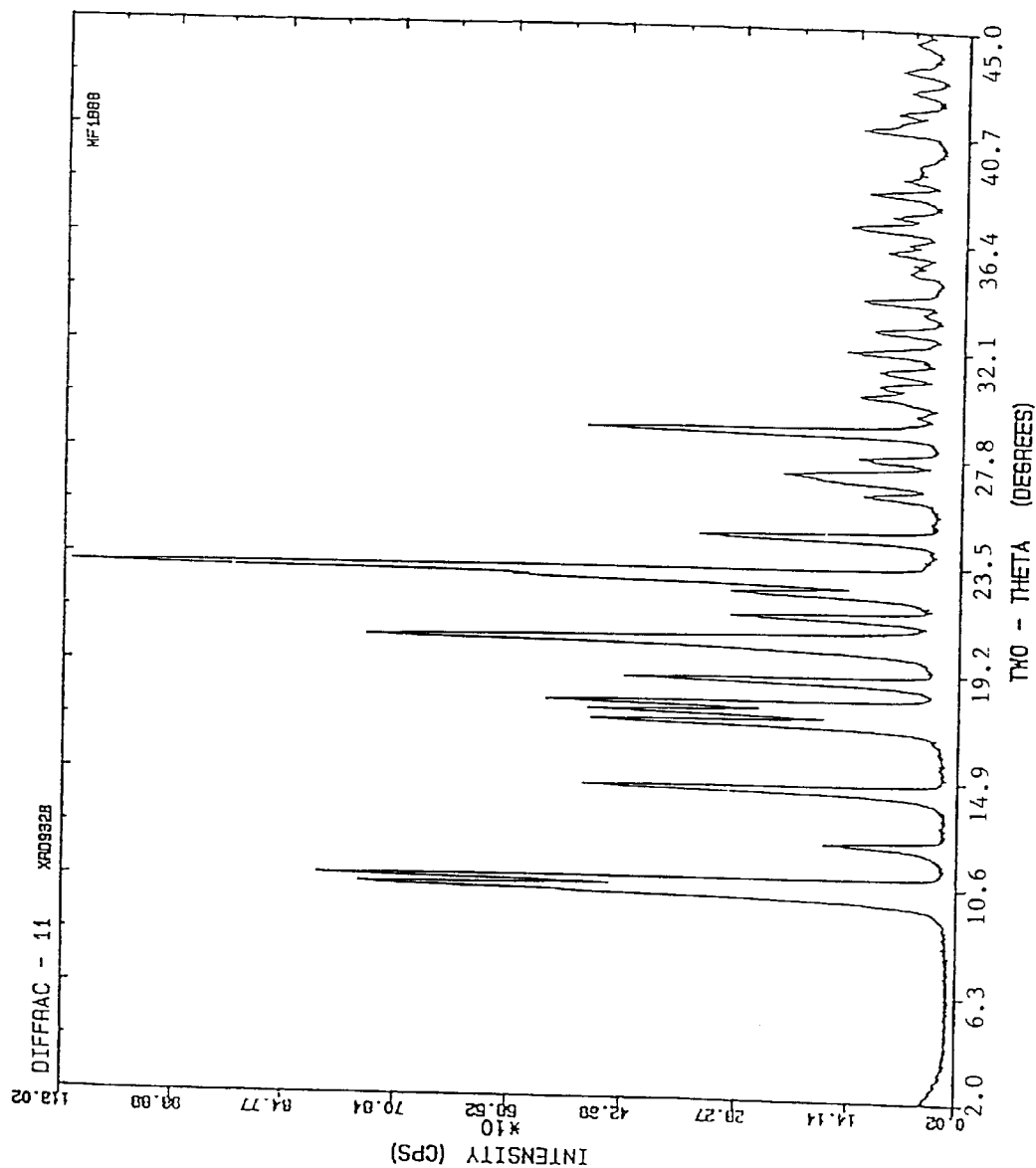
Figure 9:
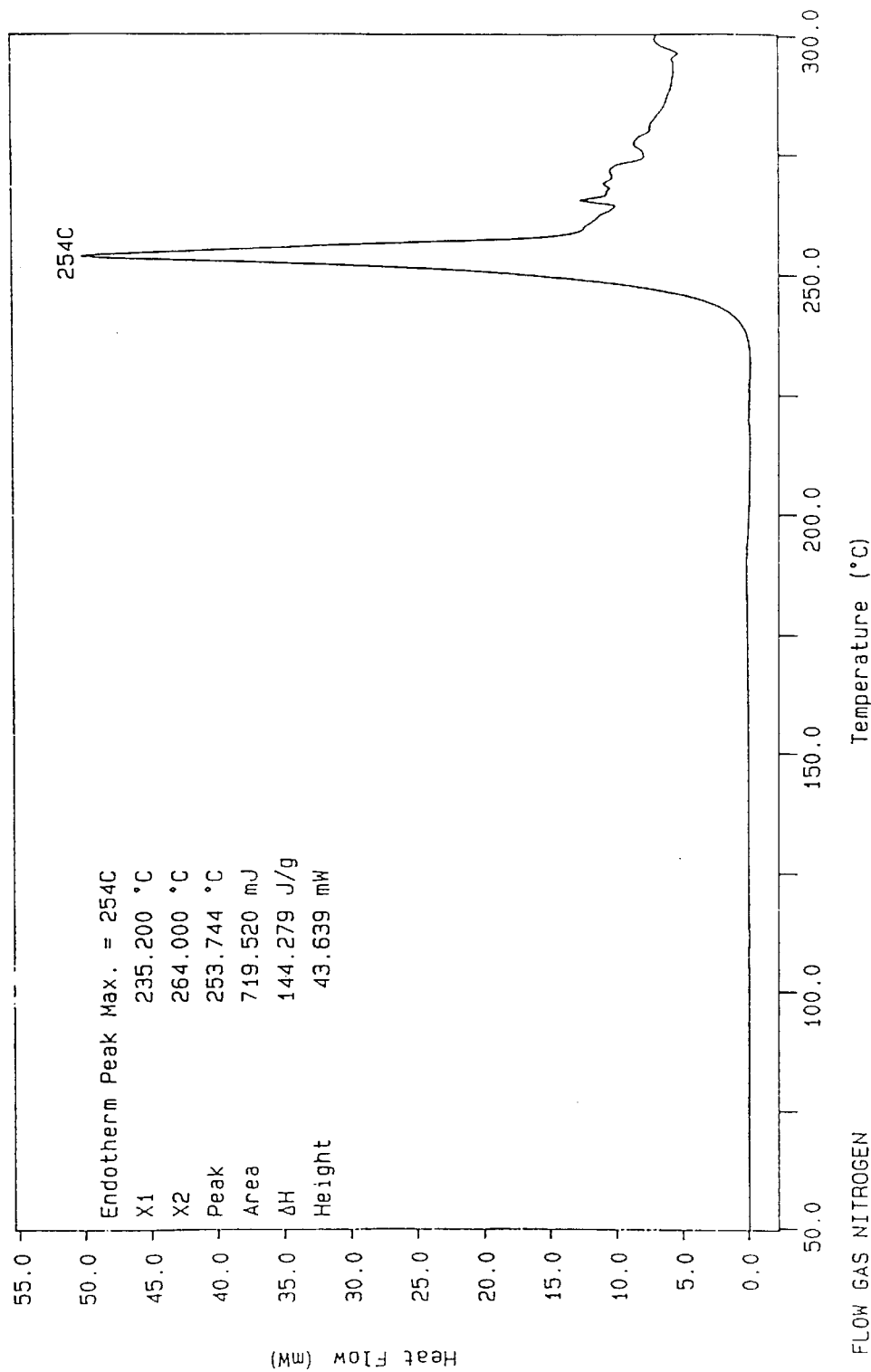
FIGS. 9–12 are DSC thermographs for certain polymorphs of (S,S,S)-N-(1-[2-carboxy-3-($N^2$-mesyllysylamino) propyl]-1-cyclopentylcarbonyl)tyrosine.
Figure 10:
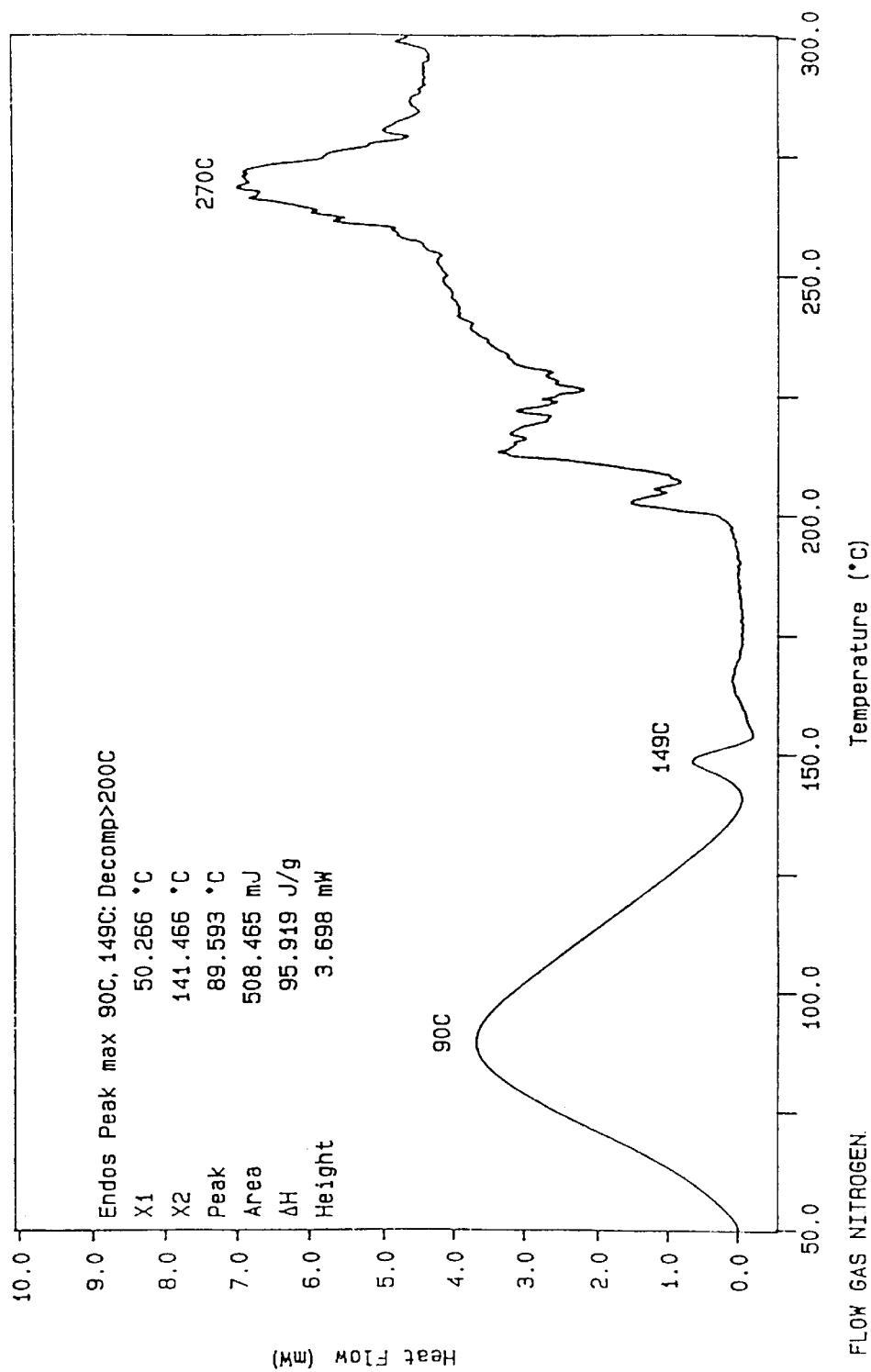
Figure 11:
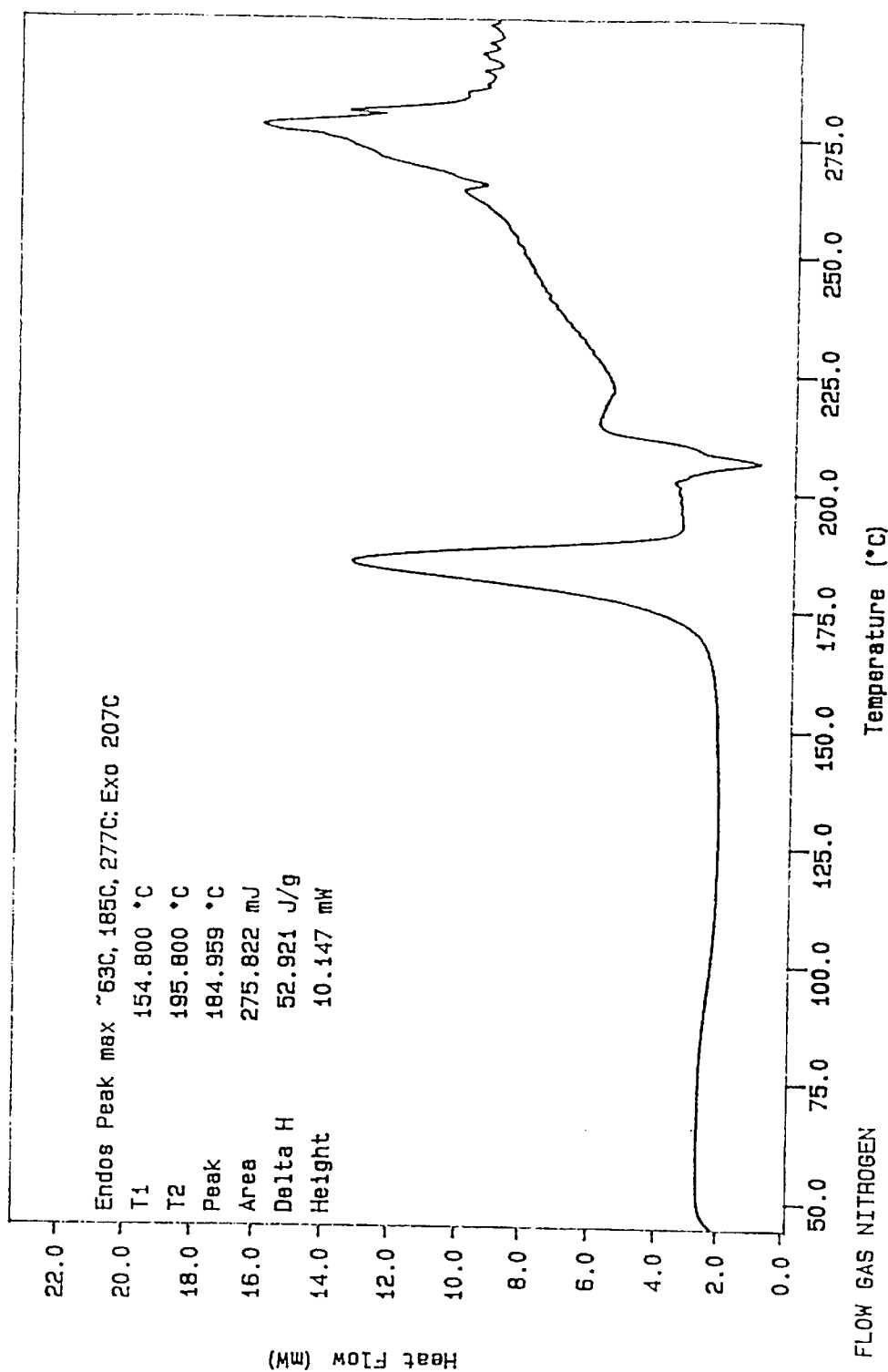
Figure 12:
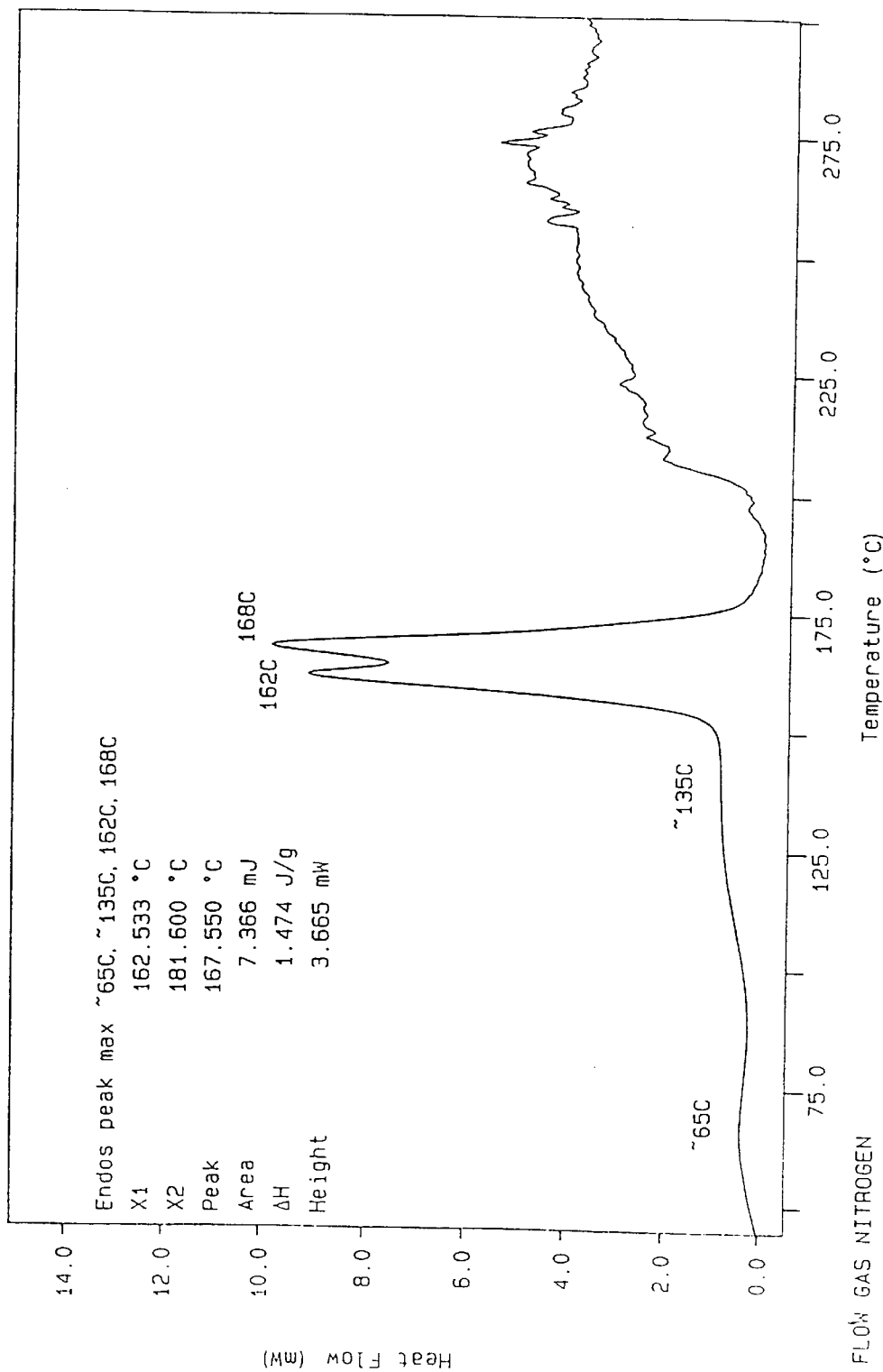

The α-form of a compound of the formula (I) can be prepared by the following methods:

1) The α-form can be prepared by catalytic hydrogenation of an aqueous solution of a sodium, potassium, ammonium or ($C_1$–$C_4$ alkyl)ammonium salt of a compound of the formula:

using a suitable catalyst for the removal of the benzyloxycarbonyl protecting group, e.g. palladium-on-carbon, followed by acidification of the base salt of the compound of the formula (I) obtained to from pH 3 to 5, preferably to about pH4, and preferably at from 35 to 45° C., to provide the α-form. Preferably a disodium salt of a compound of the formula (II) is used. Further suitable catalysts for the removal of the benzyloxycarbonyl protecting group are well known to the skilled person, e.g. see T. W. Greene and P. G. Wuts, "Protective Groups in Organic Synthesis", Second Edition, 1991, the teaching of which is incorporated herein by reference.

In a typical procedure, a solution of a compound of the formula (II) in a suitable organic solvent, e.g. ethyl acetate, is shaken with an aqueous solution of sodium hydroxide to generate a disodium salt thereof. The aqueous solution containing the sodium salt is then separated and hydrogenated in the presence of a 5% palladium-on-carbon catalyst at about 414 kPa (60 psi) and room temperature to remove the benzyloxycarbonyl protecting group. The catalyst is then removed by filtration and the filtrate adjusted to about pH 4 using a suitable acid, e.g. aqueous hydrochloric acid. The α-form is precipitated from solution and can be collected by filtration.

A compound of the formula (II) can be prepared by the route set out in Scheme 1.

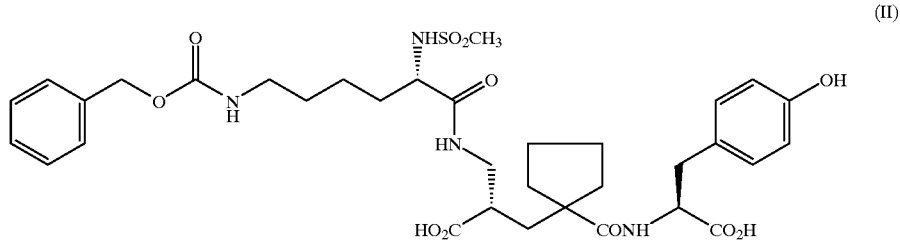

(II)

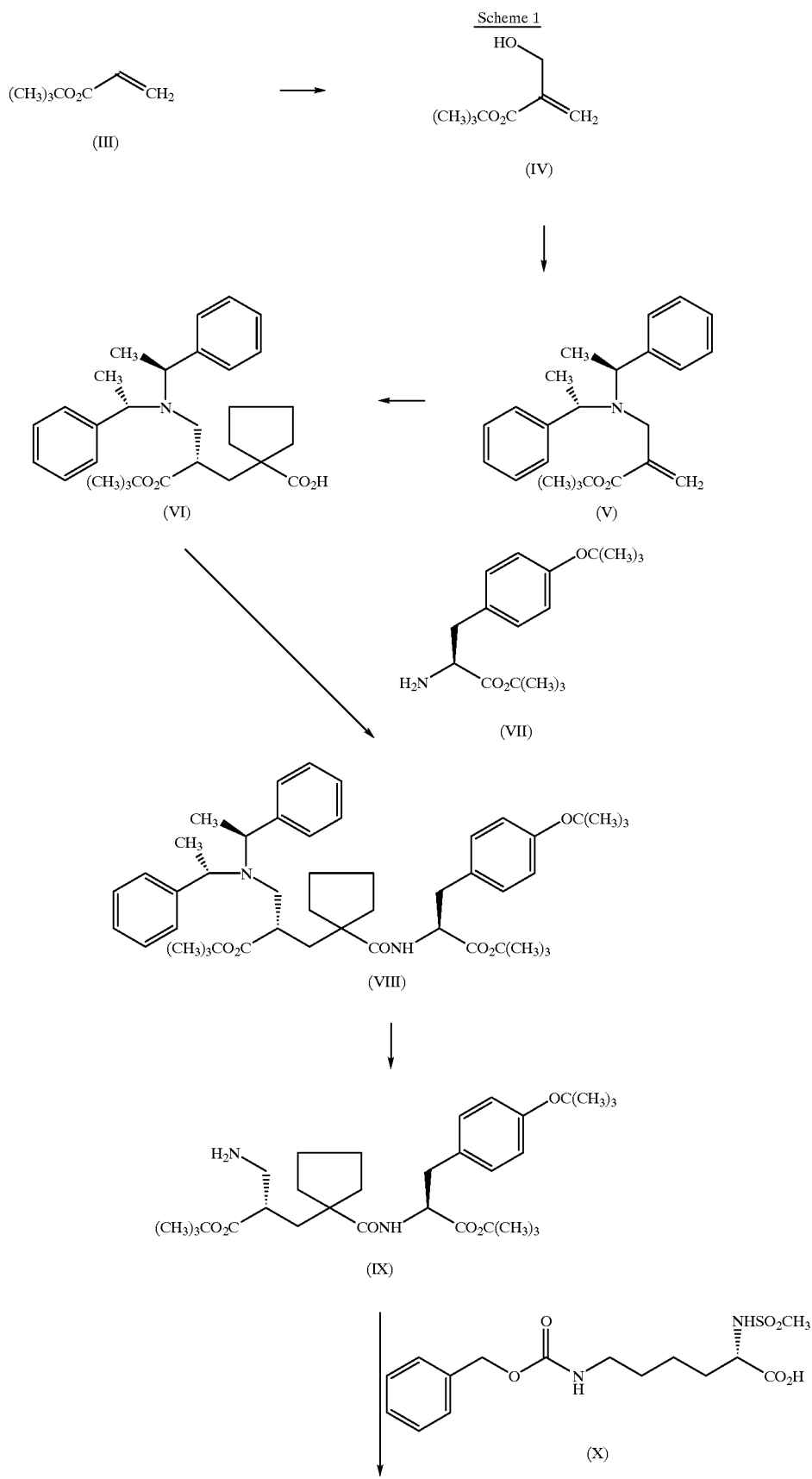
Scheme 1

-continued

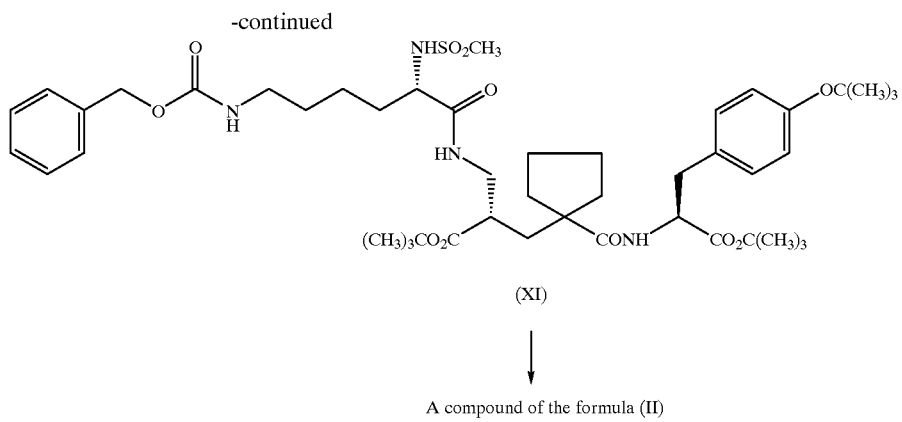

(XI)

↓

A compound of the formula (II)

In a typical procedure, t-butyl acrylate (III) is reacted with paraformaldehyde in the presence of 3-quinuclidinol to provide t-butyl hydroxymethylacrylate (IV). This is first treated with thionyl chloride in the presence of triethylamine and pyridine to provide the corresponding chloromethylacrylate, which is then reacted with (S,S)-α-α'-dimethyldibenzylamine to provide an acrylate of the formula (V). This is converted to a compound of the formula (IX) by the method set out in Tet. Lett., 1993, 34(8), 1323–6. A compound of the formula (IX) is then condensed with a lysine derivative of the formula (X) by a similar procedure to that described in EP-A-0358398 for the preparation of a compound of the formula (XI). A compound of the formula (XI) is then converted to a compound of the formula (II) using a solution of trifluoroacetic acid and anisole in dichloromethane.

2) The α-form can be prepared from the δ-form by stirring a solution of the δ-form in water or in an aqueous solution of a suitable organic solvent, e.g. a $C_1$–$C_4$ alkanol such as methanol or isopropanol, or a $C_3$–$C_6$ alkanone such as acetone.

In a typical procedure the δ-form is dissolved in a 1:5 water/methanol or a 1:10 water/acetone mixture and the solution stirred for several days at room temperature. The α-form precipitates from the solution and can be collected by filtration.

3) The α-form can be prepared from the γ-form by stirring a solution of the γ-form in water or in an aqueous solution of a suitable organic solvent, e.g. a $C_1$–$C_4$ alkanol such as methanol or isopropanol, or a $C_3$–$C_6$ alkanone such as acetone.

In a typical procedure the γ-form is dissolved in a 1:1 water/methanol mixture and the solution stirred for about 17 hours at room temperature. The α-form precipitates from the solution and can be collected by filtration.

4) The α-form can be prepared from the β-form by a similar procedure to that set out in Method (3) above.

5) The α-form can be prepared by deprotection, preferably under acidic conditions, of a compound of the formula:

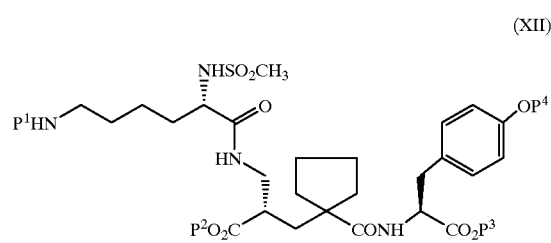

(XII)

wherein $P^1$, $P^2$, $P^3$ and $P^4$ are all suitable protecting groups that are capable of removal, preferably under acidic conditions, to provide, following adjustment of the pH to from 3 to 5, preferably about 4, in the work-up, the α-form.

Suitable protecting groups for this purpose together with conditions for their removal will be well known to the skilled person, e.g. see T. W. Greene, and P. G. Wuts, "Protective Groups in Organic Synthesis", Second Edition, Wiley-Interscience. $P^1$ is preferably formyl or benzyloxycarbonyl. $P^2$, $P^3$ and $P^4$ are preferably each t-butyl.

In a typical procedure where $P^1$ is formyl or benzyloxycarbonyl and $P^2$, $P^3$ and $P^4$ are each t-butyl, a solution of a compound of the formula (XII) in a suitable solvent, e.g. 1,4-dioxane or ethyl acetate, is treated with a suitable acid, e.g. hydrogen chloride, to remove to the protecting groups and adjustment of the pH to about 4 in the work-up provided the α-form.

The intermediates of the formula (XII) may be prepared by conventional techniques. The compound of the formula (XII) where $P^1$ is benzyloxycarbonyl and $P^2$, $P^3$ and $P^4$ are each t-butyl corresponds to the compound of the formula (XI) in Scheme 1, the synthesis of which is further described in Method (1). The compound of the formula (XII) where $P^1$ is formyl and $P^2$, $P^3$ and $P^4$ are each t-butyl may be prepared by first removing the benzyloxycarbonyl group from the compound of the formula (XI) by hydrogenolysis using a suitable catalyst, e.g. palladium-on-carbon, followed by formylation of the amine obtained, e.g. using formic acetic anhydride.

6) The α-form can be prepared by deprotection, preferably under acidic conditions, of a compound of the formula:

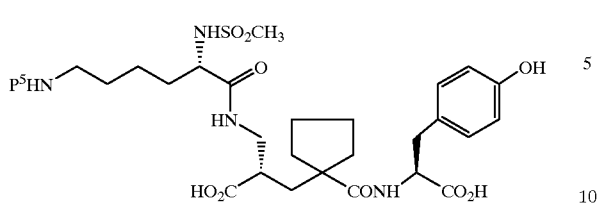

(XIII)

wherein $P^5$ is a suitable protecting group that is capable of removal, preferably under acidic conditions, to provide, following adjustment of the pH to from 3 to 5, preferably about 4, in the work-up, the α-form. Suitable protecting groups for this purpose together with conditions for their removal will be well known to the skilled person, e.g. see T. W. Greene and P. G. Wuts, "Protective Groups in Organic Synthesis", Second Edition, Wiley-Interscience. $P^5$ is preferably formyl and further examples of $P^5$ are benzyloxycarbonyl and tert-butyloxycarbonyl.

In a typical procedure where $P^5$ is formyl, a solution of a compound of the formula (XIII) in a suitable solvent, e.g. 1,4-dioxane, is treated with an aqueous solution of a suitable acid, e.g. hydrochloric acid, to remove the protecting group and adjustment of the pH to about 4 in work-up provided the α-form.

The intermediates of the formula (XIII) may be prepared by conventional techniques, such as by selective deprotection of a compound of the formula (XII) to remove the $P^2$, $P^3$ and $P^4$ protecting groups alone. For example, where $P^1$ is formyl and $P^2$, $P^3$ and $P^4$ are each t-butyl, the t-butyl protecting groups may be selectively removed by treatment of a compound of the formula (XII) with trifluoroacetic acid in a suitable solvent, e.g. dichloromethane.

The β-, γ- and δ-forms that are used as intermediates in preparing the α-form can be prepared as follows:

(i) The β-form can be prepared by catalytic hydrogenation of a solution of a compound of the formula (II) in a suitable solvent and in the presence of a suitable catalyst for the removal of the protecting group, e.g. palladium-on-carbon.

In a typical procedure, a solution of a compound of the formula (II) in aqueous ethanol is hydrogenated at about 414 kPa (60 psi) and room temperature in the presence of a palladium-on-carbon catalyst. The catalyst is then removed by filtration and the filtrate is either concentrated under reduced pressure to provide a foam that is stirred with a $C_3$–$C_6$ alkanone, e.g. acetone, or freeze dried, to provide the β-form that can be collected by filtration. This preparation has also, if the $C_3$–$C_6$ alkanone treatment is used, occasionally provided the α-form.

(ii) The δ-form can be prepared by catalytic hydrogenation of a solution of a compound of the formula (II) in a mixture of a suitable water immiscible organic solvent, e.g. ethyl acetate, and water and in the presence of a suitable catalyst for the removal of the protecting group, e.g. palladium-on-carbon, followed by removal of the catalyst, separation of the aqueous layer and precipitation of the product from the aqueous layer using a $C_1$–$C_4$ alkanol, e.g. methanol.

In a typical procedure, water is added to a solution of a compound of the formula (II) in ethyl acetate and the mixture is hydrogenated at about 414 kPa (60 psi) and room temperature in the presence of a palladium-on-carbon catalyst. The catalyst is then removed by filtration, the aqueous phase separated from the filtrate, concentrated under reduced pressure to a low volume and poured into methanol. The δ-form slowly precipitates from the solution and can be collected by filtration.

This preparation has also occasionally provided the α-form.

(iii) The β-form can be prepared by first freezing an aqueous solution of the β-form and then freeze drying the resulting solid mass.

(iv) The γ-form can be prepared by stirring the δ-form with n-propanol or acetonitrile.

In a typical procedure the mixture is stirred for about 24 hours at room temperature and the γ-form is collected by filtration.

(v) The γ-form can be prepared by stirring a slurry of the β-form in acetonitrile or n-propanol, typically for about 5 days at room temperature. The γ-form is collected by filtration.

(vi) The γ-form can be prepared by treating an aqueous solution of the δ-form with a $C_3$–$C_6$ alkanone, e.g. acetone.

In a typical procedure an aqueous solution of the δ-form is poured into a vigorously stirred volumetric excess of acetone at room temperature. The γ-form precipitates from solution and can be collected by filtration.

This preparation has also occasionally provided the α-form.

(vii) The β-form can be prepared by freeze drying a concentrated, aqueous solution of the α-form.

In a typical procedure, a concentrated solution of the α-form in hot water is prepared, the solution filtered to remove any insoluble material, then cooled, frozen and finally freeze dried to provide the β-form.

As previously mentioned, the α-form is a potent inhibitor of the neutral endopeptidase (E.C.3.4.24.11). This enzyme is involved in the breakdown of a number of peptide hormones and peptide autocoid substances including, in particular, the breakdown of atrial natriuretic factor (ANF). Thus the α-form, by preventing the degradation of ANF by neutral endopeptidase E.C.3.4.24.11, can potentiate the biological effects of ANF and is therefore a diuretic, natriuretic and antihypertensive agent of utility in the treatment of a number of disorders including hypertension, heart failure, angina, renal insufficiency, chronic renal failure, premenstrual syndrome, cyclical oedema, Menieres disease, hyperaldosteroneism (primary and secondary) and hypercalciuria. In addition, because of its ability to potentiate the effects of ANF, the α-form is useful in the treatment of glaucoma. Further, as a result of its ability to inhibit the neutral endopeptidase E.C.3.4.24.11, the α-form may be useful in treating asthma, inflammation, pain, epilepsy, affective disorders, dementia, geriatric confusion, obesity, gastrointestinal disorders (especially diarrhoea and irritable bowel syndrome) and hyperreninaemia and in the modulation of gastric acid secretion.

The activity against neutral endopeptidase E.C.3.4.24.11 can be assessed using a procedure based on the assay described by Barclay, P. L., et al, Biochem. Biophys. Res. Comm., 1989, 164, 58–65. The method involves determining the concentration of compound required to reduce by 50% the rate of release of radiolabelled hippuric acid from hippuryl-L-phenylalanyl-L-arginine by a neutral endopeptidase preparation from rat kidney.

As previously mentioned, the α-form is also an inhibitor of angiotensin converting enzyme (ACE). As such it is useful in treating a variety of conditions for which ACE inhibitors are known to be useful including hypotension, congestive heart failure, limitation of ischaemic damage to the myocardium, protection of the kidney against hyperfiltration damage, prevention or reversal of left ventricular hypertrophy, memory enhancement, control of cognitive function, dementia and preventing reocclusion following coronary angioplasty or coronary artery bypass surgery. Its activity against this enzyme can be assessed using a procedure which is based on a modification of the assay described by Rohrbach, M. S., Anal. Biochem., 1978, 84, 272. The method involves determining the concentration of compound required to reduce by 50% the extent of release of radiolabelled hippuric acid from hippuryl-L-histidyl-L-leucine by angiotensin converting enzyme isolated from the rat kidney.

Inhibitory activity can also be measured in vivo following intravenous injection to anaesthetised rats using the methods described by I. L. Natoff et al, Journal of Pharmacological Methods, 1981, 5, 305 and by D. M. Gross et al, J. Pharmacol, Exp. Ther., 1981, 216, 552. The dose of the inhibitor that is required to reduce the pressor response produced by intravenous injection of angiotensin 1 (50 ng bolus) by 50% is determined.

The activity of the α-form as a diuretic agent can be determined by measuring its ability to increase urine output and sodium ion excretion in conscious AV-blocked dogs using the methods described by Alabaster, C. T., et al, Brit. J. Pharmacol., 1989, 98, 823P.

The antihypertensive activity of the α-form can be evaluated by measuring the fall in blood pressure following oral or intravenous administration to salt depleted, diuretic primed, spontaneously hypertensive rats, salt depleted renally hypertensive dogs, or desoxycorticosterone acetate (DOCA)/salt hypertensive rats.

For administration to an animal in the treatment of hypertension, congestive heart failure or renal insufficiency, oral dosages of the α-form will generally be in the range of 1–500 mg daily, and preferably 5–200 mg daily for the treatment of human beings, for an average adult patient. Thus for a typical adult human patient, individual tablets or capsules contain from 1 to 200 mg of the compound in a suitable pharmaceutically acceptable diluent or carrier for administration singly, or in multiple doses, once or several times a day. Dosages for intravenous administration would typically be from 0.01 to 50 mg, preferably 0.1 to 10 mg, of compound per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the α-form can be administered alone, but will generally be administered in admixture with a pharmaceutically acceptable diluent or carrier selected with regard to the intended route of administration and standard pharmaceutical practice. For example, it may be administered orally in the form of tablets containing such excipients as starch or dibasic calcium phosphate, or in capsules or ovules either alone or in admixture with excipients, or in the form of an elixir or a suspension containing flavouring or colouring agents. It may be injected parenterally, for example, intravenously, intramuscularly or subcutaneously. For parenteral administration, it is best used in the form of a sterile aqueous solution which may contain other substances, for example, enough salts or glucose to make the solution isotonic with blood.

The α-form may be co-administered with other agents that are useful for the control of blood pressure, the treatment of cardiac conditions or renal insufficiency. Thus, for example, it may be co-administered with a cardiac stimulant, for example digitalis, an alpha-blocker, for example doxazosin, a beta-blocker, a calcium channel blocker, for example amlodipine, exogenous ANF, a potassium channel activator or with another diuretic agent as shall be determined by the physician with regard to the particular patient or disease state.

Therapeutic treatment by use of the α-form as disclosed herein can mean curative or prophylactic treatment of a particular disease.

The invention thus further provides:

(a) a pharmaceutical composition comprising the α-form, γ-form or hydrated δ-form of a compound of the formula (I) together with a pharmaceutically acceptable diluent or carrier.

(b) the α-form, γ-form or hydrated δ-form of a compound of the formula (I), or a pharmaceutical composition thereof, for use as a medicament.

(c) the use of the α-form, γ-form or hydrated δ-form of a compound of the formula (I), or of a pharmaceutical composition thereof, for the manufacture of a medicament for treating a disease which is dependent on the inhibition of angiotensin converting enzyme and/or zinc dependent neutral endopeptidase E.C.3.4.24.11.

(d) use as stated in (c) where the disease is a cardiovascular disorder such as hypertension, congestive heart failure, renal insufficiency or glaucoma.

(e) a method of treatment of an animal, including a human being, to treat a disease which is dependent on the inhibition of angiotensin converting enzyme and/or zinc dependent neutral endopeptidase E.C.3.4.24.11, which comprises administering to said animal a said enzyme and/or said endopeptidase inhibitory amount of the α-form, γ-form or hydrated δ-form of a compound of the formula (I) or a pharmaceutical composition thereof.

(f) a method as stated in (e) where the disease is as stated in (d).

(g) a sodium, potassium, ammonium or ($C_1$–$C_4$ alkyl) ammonium salt of a compound of the formula (II).

(h) the γ-form of a compound of the formula (I).

(i) the hydrated δ-form of a compound of the formula (I).

(j) a compound of the formula (XII) with the proviso that $P^1$ is not benzyloxycarbonyl when $P^2$, $P^3$ and $P^4$ are each t-butyl.

(k) a compound of the formula (XIII) with the proviso that $P^5$ is not benzyloxycarbonyl.

The preparation of the α-form is illustrated by the following Examples:

EXAMPLE 1

(S,S,S)-N-(1-[2-Carboxy-3-($N^2$-mesyllysylamino) propyl]-1-cyclopentylcarbonyl)tyrosine, α-form A solution of (S,S,S)-N-(1-[3-($N^6$-benzyloxycarbonyl-$N^2$-mesyllysylamino)-2-carboxypropyl]-1- cyclopentylcarbonyl)tyrosine in ethyl acetate (1190 ml) (a portion of the solution obtained according to the method of Preparation 9 and taken to contain 219 g of the starting material) was shaken with a solution of sodium hydroxide (23.1 g) in water (503 ml). The aqueous phase was separated and hydrogenated at 414 kPa (60 psi) and room temperature over a 5% palladium-on-carbon catalyst (20 g) for 5 hours. The catalyst was then filtered off and the filtrate adjusted to pH 4 with 5N aqueous hydrochloric acid solution and a white solid precipitated. After granulating for 18 hours at room temperature, the solid product was filtered, washed with water and dried to give the title compound as a white solid (124.4 g), m.p. 248–250° C. Found: C,53.47; H,7.25; N,9.50. $C_{26}H_{40}N_4O_9S$ requires: C,53.41; H,6.90; N,9.58%.

EXAMPLE 2

(S,S,S)-N-(1-[2-Carboxy-3-($N^2$-mesyllysylamino) propyl]-1-cyclopentylcarbonyl)tyrosine, α-form A solution of (S,S,S)-N-(1-[2-carboxy-3-($N^2$-mesyllysylamino)propyl]-1-cyclopentylcarbonyl)tyrosine hydrate (the δ-form, see Preparation 2) (3.0 g) in a 1:5 water/methanol mixture (18 ml) or a 1:10 water/acetone mixture (33 ml) was stirred for 3 days at room temperature. The resulting solid was collected by filtration and dried to give the title compound as a white solid, m.p. 246–8° C. (from the aqueous methanol method), m.p. 242–3° C. (from the aqueous acetone method).

EXAMPLE 3

(S,S,S)-N-(1-[2-Carboxy-3-($N^2$-mesyllysylamino) propyl]-1-cyclopentylcarbonyl)tyrosine, α-form (S,S,S)-N-(1-[2-Carboxy-3-($N^2$-mesyllysylamino) propyl]-1-cyclopentylcarbonyl)tyrosine, γ-form (see Preparations 4, 5, 7 and 8) (0.5 g) was dissolved in water (4 ml) and methanol (4 ml) was added. The resulting solution was stirred for 17 hours at room temperature. A white solid formed which was collected by filtration and dried to give the title compound (0.43 g), m.p. 250–252° C.

EXAMPLE 4

(S,S,S)-N-(1-[2-Carboxy-3-($N^2$-mesyllysylamino) propyl]-1-cyclopentylcarbonyl)tyrosine, α-form (S,S,S)-N-(1-[2-Carboxy-3-($N^2$-mesyllysylamino) propyl]-1-cyclopentylcarbonyl)tyrosine, 3-form (see Preparations 1, 3 and 6) (0.5 g) was dissolved in water (4 ml) and methanol (4 ml) was added. The resulting solution was stirred for 17 hours at room temperature. A white solid formed which was collected by filtration and dried to give the title compound (0.43 g), m.p. 249–251° C.

EXAMPLE 5

(S,S,S)-N-(1-[2-Carboxy-3-($N^2$-mesyllysylamino) propyl]-1-cyclopentylcarbonyl)tyrosine, α-form To a solution of the compound of Preparation 12 (2.50 g, 3.20 mmol) in 1,4-dioxane (20 ml) was added a solution of 1,4-dioxane (20 ml) saturated with HCl gas. After 30 minutes, the initially clear solution deposited an oil which was stirred for 24 hours at room temperature. Water (20 ml) was added to give a clear solution which was stirred at room temperature for 60 hours. Evaporation of the resulting solution under reduced pressure gave an oil which was dissolved in water and basified with aqueous sodium hydroxide solution until pH 4 was obtained. The solvent was removed by evaporation under reduced pressure and granulation of the resultant material with methanol provided an off-white solid which was collected by filtration and reslurried in water (4 ml) overnight. The solids were filtered off and dried to yield the title compound (0.97 g), m.p. 225–230° C. IR and PXRD analysis confirmed the product to be the required α-form.

EXAMPLE 6

(S,S,S)-N-(1-[2-Carboxy-3-($N^2$-mesyllysylamino) propyl]-1-cyclopentylcarbonyl)tyrosine, α-form To a solution of the compound of Preparation 13 (1.78 g) in 1,4-dioxane (18 ml) was added aqueous 4M hydrochloric acid (18 ml). The clear yellow solution was allowed to stir at room temperature for 60 hours followed by an additional 18 hours at 35° C. Removal of the solvent under reduced pressure gave 5.42 g of material, 4.22 g of which was dissolved in water (10 ml), the solution basified with aqueous sodium hydroxide solution to pH 4.0, seeded with the compound of Example 1 and stirred at room temperature for 18 hours. The resulting clear solution was concentrated to about 10 ml in volume under reduced pressure, diluted with methanol (15 ml) and granulated for 48 hours. The solids were collected by filtration and dried to provide the title compound (1.25 g), m.p. 232–235° C.

IR and PXRD analysis confirmed the product to be the required α-form.

EXAMPLE 7

(S,S,S)-N-(1-[2-Carboxy-3-($N^2$-mesyllysylamino) propyl]-1-cyclopentylcarbonyl)tyrosine, α-form To a cooled (10° C.) solution of tert-butyl (S,S,S)-N-(1-[3-($N^6$-benzyloxycarbonyl-$N^2$-mesyllysylamino)-2-(tert-butoxycarbonyl)propyl]-1-cyclopentylcarbonyl)-$O^4$-tert-butyltyrosinate (13.3 g, 15.0 mmol) in ethyl acetate (27 ml) was added a 5.1M solution of hydrogen chloride in ethyl acetate (70 ml) (357 mmol of HCl). After 30 minutes the initially clear solution deposited a tar. The mixture was stirred at room temperature for 18 hours. The clear solution was decanted off from the tar and the tar triturated with ethyl acetate (75 ml) to give a sticky solid. The decantation and trituration were repeated 5 times to give a hygroscopic solid which was dissolved in water (12 ml). The resulting aqueous solution was washed twice with ethyl acetate, basified with aqueous sodium hydroxide solution to pH 4.0, seeded with the compound of Example 1 and stirred at 45–50° C. for 42 hours. The off-white solids were collected by filtration, washed with water and acetone and dried to give the title compound (1.95 g), m.p. 237–238° C.

IR and PXRD analysis confirmed the product to be the required α-form.

The following Preparations illustrate the preparation of certain intermediate compounds used in synthesising the α-form:

PREPARATION 1

(S,S,S)-N-(1-[2-Carboxy-3-($N^2$-mesyllysylamino) propyl]-1-cyclopentylcarbonyl)tyrosine, β-form A solution of (S,S,S)-N-(1-[3-($N^6$-benzyloxycarbonyl-$N^2$-mesyllysylamino)-2-carboxypropyl]-1-cyclopentylcarbonyl)tyrosine (see Preparation 9) (371 g) in a 9:1 ethanol/water mixture (2.225 l) was hydrogenated at 414 kPa (60 psi) and room temperature over a 10% palladium-on-carbon catalyst (37.0 g) for 4 hours. The catalyst was filtered off and the filtrate evaporated to leave the crude product as a foam. This material was stirred with acetone (3.13 l) for 24 hours to give the title compound as a white amorphous solid (283 g). Found: C,52.97; H,7.02; N,8.97. $C_{26}H_{40}N_4O_9S$ requires: C,53.41; H,6.90; N,9.58%.

PREPARATION 2

(S,S,S)-N-(1-[2-Carboxy-3-($N^2$-mesyllysylamino) propyl]-1-cyclopentylcarbonyl)tyrosine hydrate (the δ-form)

A solution of (S,S,S)-N-(1-[3-($N^6$-benzyloxycarbonyl-$N^2$-mesyllysylamino)-2-carboxypropyl]-1-cyclopentylcarbonyl)tyrosine (see Preparation 9) (351 g) in ethyl acetate (1300 ml) was added to water (385 ml) and the two phase mixture hydrogenated at 414 kPa (60 psi) and room temperature over a 5% palladium-on-carbon catalyst (35 g) for 20 hours. The catalyst was filtered off, the aqueous phase separated and concentrated to low volume under reduced pressure. The viscous solution was poured into methanol (2.85 l) and stirred at room temperature for 18 hours during which time there was a slow precipitation of a solid. The solid was granulated at 5–10° C. for 2 hours, filtered, washed with methanol and dried to give the title compound as a white solid (178.1 g), m.p. 168–171° C. Found: C,51.37; H,7.47; N,9.06. $C_{26}H_{40}N_4O_9S \cdot \chi H_2O$ (where $\chi$=1) requires: C,51.81; H,7.02; N,9.30%.

Water content=3.6% by weight as determined by Karl Fischer analysis ($\chi$=1 requires 3.0% by weight).

PREPARATION 3

(S,S,S)-N-(1-[2-Carboxy-3-($N^2$-mesyllysylamino) propyl]-1-cyclopentylcarbonyl)tyrosine, β-form (S,S,S)-N-(1-[2-Carboxy-3-($N^2$-mesyllysylamino) propyl]-1-cyclopentylcarbonyl)tyrosine hydrate (the δ-form, see Preparation 2) (20.0 g) was dissolved in water (250 ml) at room temperature and the clear solution frozen using a solid carbon dioxide/acetone bath. The solid mass was freeze dried to yield the title compound as a white solid (19.0 g). This material decomposed slowly over the temperature range 155–170° C.

PREPARATION 4

(S,S,S)-N-(1-[2-Carboxy-3-($N^2$-mesyllysylamino) propyl]-1-cyclopentylcarbonyl)tyrosine, γ-form (S,S,S)-N-(1-[2-Carboxy-3-($N^2$-mesyllysylamino) propyl]-1-cyclopentylcarbonyl)tyrosine hydrate (the δ-form, see Preparation 2) (1.0 g) was stirred with either n-propanol or acetonitrile (10 ml) for 24 hours at room temperature. In each case the white solid obtained was collected by filtration and dried to provide the title compound, m.p. 172–176° C.

PREPARATION 5

(S,S,S)-N-(1-[2-Carboxy-3-($N^2$-mesyllysylamino) propyl]-1-cyclopentylcarbonyl)tyrosine, γ-form (S,S,S)-N-(1-[2-Carboxy-3-($N^2$-mesyllysylamino) propyl]-1-cyclopentylcarbonyl)tyrosine hydrate (the δ-form, see Preparation 2) (847.0 g) was dissolved in water (762 ml) and the solution diluted with acetone (1.0 l). This solution was added slowly to vigorously stirred acetone (18.05 l) at room temperature and a white solid precipitated. The mixture was stirred at room temperature for 18 hours, the solid was collected by filtration, washed with acetone and dried to give the title compound as a white solid (775 g), m.p. 179–181° C. Found: C,53.42; H,6.88; N,9.37; S,5.49. $C_{26}H_{40}N_4O_9S$ requires: C,53.41; H,6.90; N,9.58; S,5.48%.

PREPARATION 6

(S,S,S)-N-(1-[2-Carboxy-3-($N^2$-mesyllysylamino) propyl]-1-cyclopentylcarbonyl)tyrosine, β-form (S,S,S)-N-(1-[2-Carboxy-3-($N^2$-mesyllysylamino) propyl]-1-cyclopentylcarbonyl)tyrosine, α-form (see Examples 1 to 4) (4.0 g) was added to water (200 ml) and the mixture stirred at 90–95° C. for 30 minutes. Insoluble material was filtered off, the filtrate diluted with further water (50 ml) and cooled to room temperature. After filtration to remove a slight haze, the clear filtrate was frozen using a solid carbon dioxide/acetone bath. The solid mass obtained was freeze dried to yield the title compound as a white solid (3.0 g). This material decomposed slowly over the temperature range 155–165° C.

PREPARATION 7

(S,S,S)-N-(1-[2-Carboxy-3-($N^2$-mesyllysylamino) propyl]-1-cyclopentylcarbonyl)tyrosine, γ-form (S,S,S)-N-(1-[2-Carboxy-3-($N^2$-mesyllysylamino) propyl]-1-cyclopentylcarbonyl)tyrosine, β-form (see Preparations 1, 3 and 6) (0.3 g) was slurried in acetonitrile (15 ml) and stirred for 5 days. The resulting white solid was collected by filtration and dried under reduced pressure to provide the title compound (0.26 g).

PREPARATION 8

(S,S,S)-N-(1-[2-Carboxy-3-($N^2$-mesyllysylamino) propyl)-1-cyclopentylcarbonyl)tyrosine, γ-form (S,S,S)-N-(1-[2-Carboxy-3-($N^2$-mesyllysylamino) propyl)-1-cyclopentylcarbonyl)tyrosine, β-form (see Preparations 1, 3 and 6) (0.3 g) was slurried in n-propanol (10 ml) and stirred for 5 days. The resulting white solid was collected by filtration and dried under reduced pressure to provide the title compound (0.26 g), m.p. 175–180° C.

PREPARATION 9

(S,S,S)-N-(1-[3-($N^6$-Benzyloxycarbonyl-$N^2$-mesyllysylamino)-2-carboxypropyl]-1-cyclopentylcarbonyl)tyrosine Tert-butyl (S,S,S)-N-(1-[3-($N^6$-benzyloxycarbonyl-$N^2$-mesyllysylamino)-2-(tert-butoxycarbonyl)propyl]-1-cyclopentylcarbonyl)-$O^4$-tert-butyltyrosinate (404 g) was dissolved in dichloromethane (810 ml). Anisole (769 g) was added in one portion and then trifluoroacetic acid (1.158 kg) added dropwise over approximately 10 minutes. On completion of the addition, the reaction was stirred at 35° C. for 6 hours and then stirred at room temperature overnight. Water (1000 ml) was added and three layers formed. The top and bottom layers were combined, dissolved in ethyl acetate (2 l) and the resulting solution washed with brine. The organic phase was mixed with brine, the pH adjusted to 3 and the layers allowed to separate. Three layers formed. The organic phases were separated, taken up in ethyl acetate and extracted with saturated aqueous sodium bicarbonate (1.6 l) solution and brine (0.5 l). The combined aqueous layers were washed with ethyl acetate, then acidified and extracted with ethyl acetate to give an ethyl acetate solution (1.54 l) of the title compound. This solution was either used directly (e.g. see Example 1) or the solvent removed to provide the title compound.

PREPARATION 10

(S)-$N^6$-Benzyloxycarbonyl-$N^2$-mesyllysine (S)-$N^6$-Benzyloxycarbonyllysine (1.5 kg) was slurried in methylene chloride (7.5 l) and chlorotrimethylsilane (1.36 l) added over 10 minutes. The mixture was heated under reflux for 30 minutes to give a solution which was cooled to 3° C. before simultaneously adding diisopropylethylamine (1.87 l) and methanesulphonyl chloride (435 ml) at such a rate as to keep the temperature below 25° C. The reaction was stirred for a further 2.5 hours then poured into 2 M aqueous hydrochloric acid solution. The layers were separated and the methylene chloride phase was washed with 2 M aqueous hydrochloric acid solution followed by water. The solvent was removed under reduced pressure and replaced with n-butyl acetate. The solution was cooled and the resulting crystalline material was collected by filtration, washed with n-butyl acetate and dried under reduced pressure to provide the title compound (1.63 kg), m.p. 83.5–84° C. $[\alpha]_D^{25}$ –13.4° (c=1, methanol). Found: C,50.23; H,6.40; N,7.76.

$C_{15}H_{22}N_2O_6S$ requires: C,50.27; H,6.19; N,7.82%. $^1$H-NMR (300 MHz, $d_6$-DMSO): δ=1.23–1.78(6H,m), 2.85 (3H,s), 2.98(2H,q), 3.80(1H,dt), 5.00(2H,s), 7.25(1H,t), 7.30–7.43(5H,m), 7.51(1H,d) ppm.

PREPARATION 11

Tert-butyl (S,S,S)-N-(1-[2-tert-butoxycarbonyl-3-($N^2$-mesyllysylamino)propyl]-1-cyclopentylcarbonyl)-$O^4$-tert-butyltyrosinate To a solution of tert-butyl (S,S,S)-N-(1-[3-($N^6$-benzyloxycarbonyl-$N^2$-mesyllysylamino)-2-(tert-butoxycarbonyl)propyl]-1-cyclopentylcarbonyl)-$O^4$-tert-butyltyrosinate (48.64 g, 54.8 mmmol) in industrial methylated spirits (1.0 L) was added 5% palladium-on-carbon (5 g) (water wet) and the mixture was hydrogenated at 345–414 kPa (50–60 psi) and at room temperature for 19 hours. After removal of the catalyst by filtration, the resulting solution was concentrated under reduced pressure to provide the title compound as a colourless oil (46.56 g) which contained ethanol.

$^1$H-NMR (300 MHz, $CDCl_3$): δ=1.27(9H,s), 1.41(9H,s), 1.44(9H,s), 1.45–1.62(14H, broad m), 1.8–2.05(4H, broad m), 2.21(2H,m), 2.72(2H,t), 2.79(3H, broad), 2.96(3H,s), 3.1(2H,m), 3.59(1H,m), 3.96(1H,t), 4.73(1H,m), 6.43(1H, dt), 6.89(2H,dt), 7.09(2H,dt), 7.51(1H,dt) ppm.

PREPARATION 12

Tert-butyl (S,S,S)-N-(1-[2-tert-butoxycarbonyl-3-($N^6$-formyl-$N^2$-mesyllysylamino)propyl]-1-cyclopentylcarbonyl)-$O^4$-tert-butyltyrosinate A cooled (0° C.) solution of formic acetic anhydride in acetic acid (made by combining 45.3 ml of acetic anhydride with 22.8 ml of formic acid, heating the resulting solution to 50–60° C. for 15 minutes, then cooling to 0° C.) was added to a solution of the compound of Preparation 11 (27.3 g, 36.3 mmol) in formic acid (33.7 ml) at 0° C. over 10 minutes. The solution was allowed to warm to and stirred at room temperature for 45 minutes and then quenched onto ice. The resulting mixture was neutralised with aqueous sodium hydroxide solution and extracted with dichloromethane (x 2). The combined organic layers were washed twice with brine and evaporated under reduced pressure to provide the title compound as a yellow foam (28.0 g).

$^1$H-NMR (300 MHz, $CDCl_3$): δ=1.26(9H,s), 1.41(18H,s), 1.45–2.03(16H, broad), 2.23(2H, broad m), 2.97(3H,s), 3.08 (2H,m), 3.28(2H,m), 3.51(1H,m), 3.98(1H, broad m), 4.73 (1H,q), 5.57(1H, broad dt), 5.91(1H, broad), 6.32(1H,dt), 6.90(2H,dt), 7.08(2H,dt), 7.29(1H,broad), 8.17(1H,s) ppm.

PREPARATION 13

(S,S,S)-N-(1-[2-Carboxy-3-($N^6$-formyl-$N^2$-mesyllysylamino)propyl]-1-cyclopentylcarbonyl) tyrosine To a cooled (0° C.) solution of the compound of Preparation 12 (2.71 g, 3.46 mmol) in dichloromethane (4.8 ml) was added trifluoroacetic acid (4.8 ml). The reaction was allowed to warm to room temperature and stirred for 24 hours. The mixture was then concentrated under reduced pressure to provide the title compound as a solid (2.4 g), m.p. 56–60° C.

$^1$H-NMR (300 MHz, $d_6$-DMSO): δ=1.2–1.6(14H, broad m), 1.71–1.86(3H,m), 1.86–1.99(1H,m), 2.28–2.41(1H,m), 2.78(3H,s), 2.8–3.09(4H,m), 3.12–3.25(2H,m), 3.7(1H,m), 4.35(1H,m), 6.6(2H,dt), 6.98(2H,dt), 7.25(1H,dt), 7.50(1H, dt), 7.91(2H,m), 7.97(1H,s) ppm.

Characterisation of the α-, β-, γ- and δ-forms by IR, PXRD and DSC Analysis and by Melting Point Determination a) Infra-red Spectroscopy (IR)

The infra-red spectra of the different forms were determined as nujol mulls using a Nicolet 800 FT-IR spectrometer. For each form, the wave numbers (v [$cm^{-1}$]) of the absorption bands are listed in Table 1.

TABLE 1

| α-form | β-form | γ-form | δ-form |
|---|---|---|---|
|  |  |  | 3667* |
| 3407* |  |  | 3425* |
| 3386* | 3384 | 3377 | 3380 |
| 3223 |  | 3240 | 3287 |
| 3153 |  |  | 3137 |
|  |  |  | 3098 |
|  | 1708 |  | 1709 |
| 1699 |  |  |  |
|  |  |  | 1673* |
| 1652* |  | 1665* |  |
|  | 1638 | 1639 | 1637 |
| 1626 |  |  |  |
|  | 1615 |  | 1619 |
| 1594 | 1595 | 1594 | 1596 |
|  |  |  | 1568 |
|  |  |  | 1556 |
|  | 1533 |  |  |
|  |  | 1527 |  |

TABLE 1-continued

| α-form | β-form | γ-form | δ-form |
|---|---|---|---|
| 1516 | 1516 | 1518 | 1516 |
|  |  | 1494* |  |
| 1457 | 1458 | 1457 | 1458 |
| (nujol) | (nujol) | (nujol) | (nujol) |
|  |  | 1443 | 1448 |
|  |  |  | 1419 |
|  | 1396 |  | 1390 |
| 1377 | 1378 | 1377 | 1378 |
| (nujol) | (nujol) | (nujol) | (nujol) |
|  |  |  | 1356 |
| 1344 |  | 1344 |  |
| 1334 |  |  | 1338 |
|  |  | 1321 |  |
| 1317 | 1313 |  |  |
|  |  | 1304 | 1300 |
|  |  |  | 1270 |
| 1267 |  |  |  |
|  |  | 1254 |  |
| 1241 | 1245 |  | 1249 |
| 1228 |  |  | 1229 |
| 1210 |  |  |  |
|  |  | 1195 | 1198 |
|  | 1172 | 1178 | 1174 |
| 1164 |  | 1162 |  |
| 1151* |  |  |  |
|  | 1144 | 1143 | 1141 |
| 1137 |  |  |  |
| 1118 |  | 1111 |  |
| 1109 | 1106 |  | 1108 |
| 1093 |  | 1098 | 1091 |
| 1074 |  |  | 1075 |
|  |  |  | 1064 |
| 1045 |  | 1046 | 1045 |
|  |  | 1031 | 1033 |
| 1019 |  | 1012 | 1019 |
| 1003 |  |  | 1001 |
| 981 | 980 |  | 985 |
|  |  | 972 |  |
| 965 |  | 962 | 962 |
|  |  | 945 | 941 |
|  |  | 932 |  |
| 911 |  |  |  |
|  |  | 907 | 909 |
| 897* |  |  |  |
|  | 889 |  | 889 |
|  |  | 879 | 877 |
| 862 |  |  |  |
|  |  | 849 | 841 |
|  | 830 |  |  |
|  |  |  | 822 |
| 818 |  | 815 |  |
| 800 | 808 | 806 | 807 |
|  |  | 780 |  |
| 778 |  |  |  |
| 762 |  |  | 763 |
|  |  | 753 |  |
|  |  |  | 744 |
|  | 737 |  | 732 |
| 721 | 721 | 729 | 721 |
|  | 665 |  |  |
| 655 |  | 658 | 655 |

*indicates those bands which are considered to be the most significant in terms of differentiating between the various forms.

Representative infra-red spectra for the various forms are shown in FIGS. 1A, 1B, 2A, 2B, 3A, 3B, 4A and 4B.

(b) Powder X-ray Diffraction (PXRD)

The powder X-ray diffraction patterns of the various forms were obtained using a Siemens D500 diffractometer that was operated at 40 kV/30 mA and using copper radiation filtered with a graphite monochromator ($\lambda$=0.15405 nm) and a scintillation counter detector. For each form, beam intensity as a function of the angle 2θ was recorded over the range 20° to 45° 2θ using a step scan mode counting for six seconds at step intervals of 0.03° 2θ. For each form, the main peaks (degrees 2θ) seen in the pattern are listed in Table 2.

TABLE 2

| α-form (sharp peaks) | (β-form) | γ-form (sharp peaks) | δ-form (sharp peaks) |
|---|---|---|---|
| 7.5 |  |  |  |
| 8.9 |  |  |  |
| 9.9 | Broad peaks with centres at 11 and 20 | 9.0, 9.6 |  |
|  |  | 10.6 | 10.5, 10.8 |
| 11.6 |  | 11.6 |  |
|  |  | 12.7 | 12.3 |
|  |  | 13.3 |  |
|  |  | 14.6 | 14.5 |
| 15.6 |  |  |  |
|  |  | 16.2 |  |
| 17.2, 17.5 |  | 17.9 | 17.2, 17.6, 17.9 |
| 18.0 |  | 18.8 | 18.9 |
| 20.2 |  | 20.2 | 20.4 |
|  |  | 21.8 | 21.5 |
| 22.1 |  |  | 22.4 |
| 23.3 |  |  | 23.0, 23.1 |
|  |  |  | 24.7 |
|  |  |  | 27.1, 27.8 |
|  |  |  | 28.9 |

Representative powder X-ray diffraction patterns for the various forms are shown in FIGS. 5 to 8.

(c) Differential Scanning Calorimetry (DSC)

Samples (about 5 mg) of the various forms were analysed using a Perkin-Elmer 7 Series thermal analyser at a scanning rate of 20° C. per minute. The results obtained for the various forms are summarised in Table 3.

TABLE 3

| Form | Summary of DSC analysis |
|---|---|
| α-form | Sharp endotherm in the range 248–259° C. Decomposition above 260° C. |
| β-form | Broad endotherm in the range 60–130° C. Weak endotherm at about 147° C. Decomposition above 200° C. |
| γ-form | Sharp endotherm in the range 176–186° C. Sharp exotherm at about 207° C. Weak endotherm at about 213° C. Decomposition above 250° C. |
| δ-form | Sharp endotherms at about 162 and at about 166–168° C. Decomposition above 200° C. |

Representative DSC thermograms for the various forms are shown in FIGS. 9 to 12.

(d) Melting Point

The melting points of the various forms were determined by hot stage microscopy using a Mettler FP5/FP52 apparatus at a heating rate of 2° C. per minute. The typical ranges within which the various forms melt are set out in Table 4.

TABLE 4

| Form | Sharp melting points in the range (° C.) |
|---|---|
| α-form | 242–252 |
| γ-form | 170–185 |
| δ-form | 165–175 |

Comparative Studies

The α- and β-forms were compared using processing and hygroscopicity studies.

(a) Processing Study

An instrumented tablet machine (Manesty Machines Limited, Model F3) was satisfactorily calibrated for force and upper punch displacement.

Figure 13:
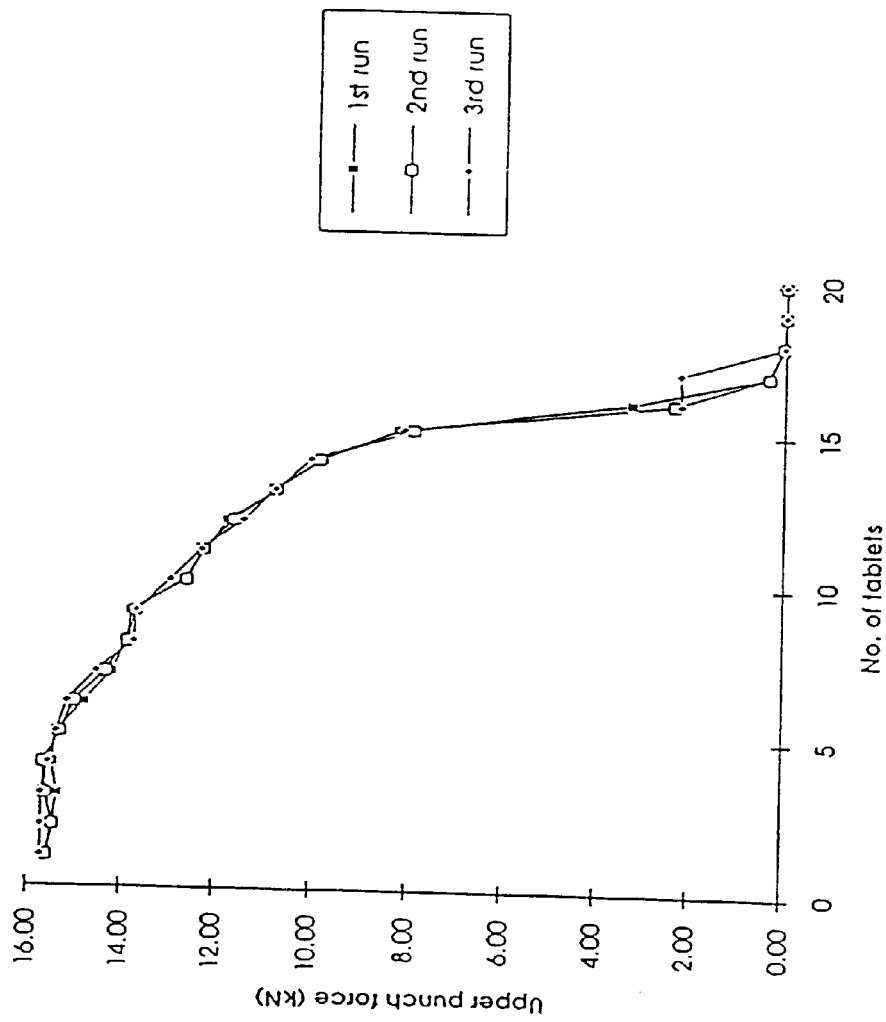
FIGS. 13–15 describe processing data for certain polymorphs of (S,S,S)-N-(1-[2-carboxy-3-($N^2$-mesyllysylamino)propyl]-1-cyclopentylcarbonyl)tyrosine.

When calibrated, a placebo Avicel (trade mark)/DCP (dibasic calcium phosphate) blend was processed on the machine using 13 mm flat faced punches to measure the reproducibility of the technique. Using an aliquot of the blend, the machine was adjusted appropriately to achieve the target compression weight (400 mg) and sufficient hardness. Twenty unit aliquots were then separately weighed and loaded into the shoe of the machine. The machine was operated under power until the blend in the shoe had been exhausted and no further tablets were produced. FIG. 13 shows a plot of upper punch force as a function of the number of tablets for three Avicel/DCP placebo blends, each of twenty units, and Table 5 shows the mean weight and hardness of the ten heaviest tablets (assumed to be the first ten produced). It can be seen from the data presented in FIG. 13 that the overall process, for this blend, was very reproducible. The decrease in upper punch force that occurred at the end of the run can be correlated with the reduction in the amount of blend in the shoe and consequential poor filling of the die.

TABLE 5

Table showing the mean weight and hardness of tablets produced using an Avicel/DCP placebo blend.

| Run | Mean weight (mg) | Standard Deviation | Mean hardness (kPa) | Standard Deviation |
|---|---|---|---|---|
| 1 | 394.3 | 7.82 | 16.0 | 1.68 |
| 2 | 389.6 | 9.20 | 14.6 | 2.04 |
| 3 | 393.3 | 6.93 | 15.1 | 1.22 |

Following the experiment to determine the reproducibility of the technique, blends containing the α-form or the β-form were separately prepared according to the following formulation: α- or β-form (100 mg), pregelatinsed starch (40 mg), dibasic calcium phosphate (anhydrous grade) (256 mg) and magnesium stearate (2 mg). A blend/screen/blend process was used to manufacture 20 g of the blend prior to slugging on the machine. The loading was 100 mg as previous experience had indicated that the higher the loading, the more processing difficulties that were encountered. The machine was adjusted for the blend and then 50 tablets were produced from the particular blend in one continuous batch.

Optimisation of the machine was more difficult with the β-form blend due to its poor flow properties. Despite careful manipulation of the process variables, it was not possible to maintain the upper punch force constant between both blends and consequently the β-form blend was compressed to a greater hardness.

Figure 14:
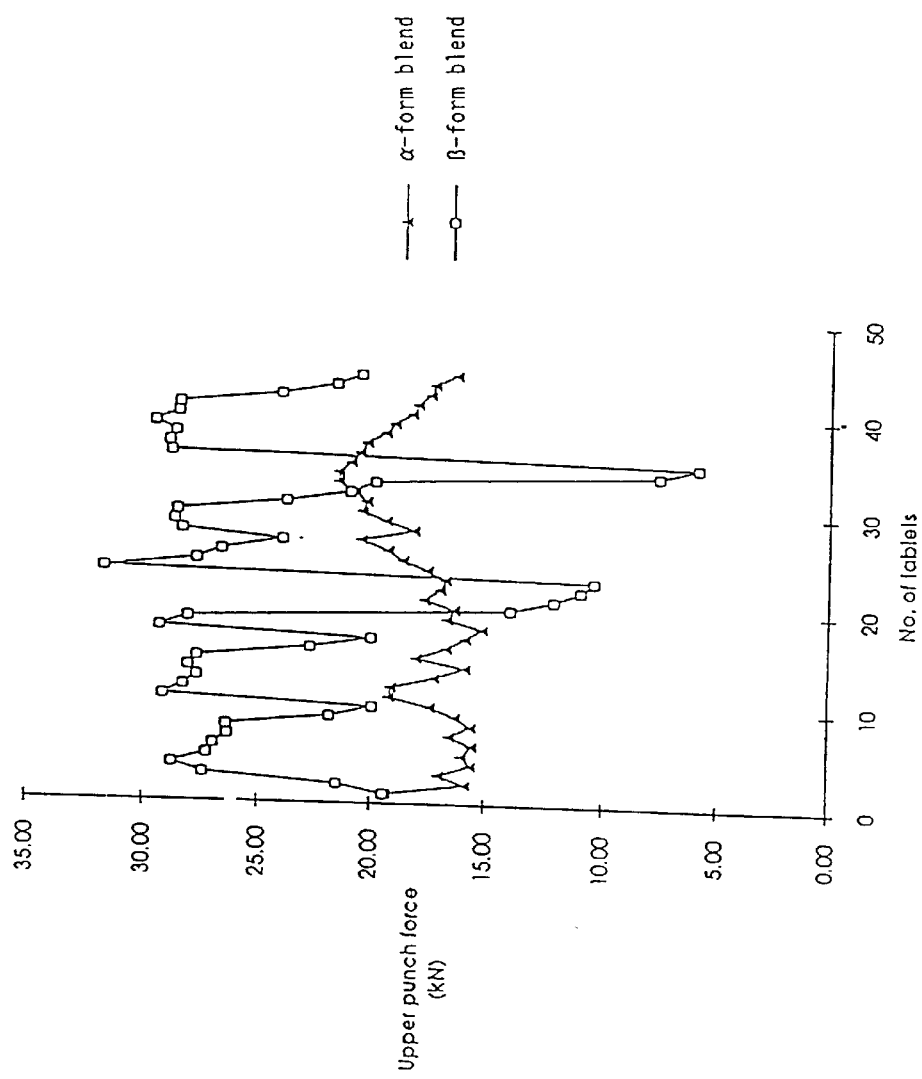

The upper punch data are shown for both blends in FIG. 14. The large variability in upper punch force (and tablet weight) for the β-form blend was associated with the non-uniform filling of the die for this formulation. The data presented in Table 6 confirms that processing of the β-form formulation was much more difficult and was subject to much greater variability than if the α-form formulation was used.

TABLE 6

Table showing the variability in processing parameters for blends containing the α- and β-forms.

| Sample | Mean upper punch force (kN) | Standard Deviation | Mean tablet weight (mg) | Standard Deviation | Mean hardness (kP) | Standard Deviation |
|---|---|---|---|---|---|---|
| α-form blend | 18.0 | 1.85 | 398 | 17.6 | 5.0 | 1.15 |
| β-form blend | 23.2 | 7.07 | 446 | 48.7 | 18.5 | 4.69 |

Figure 15:
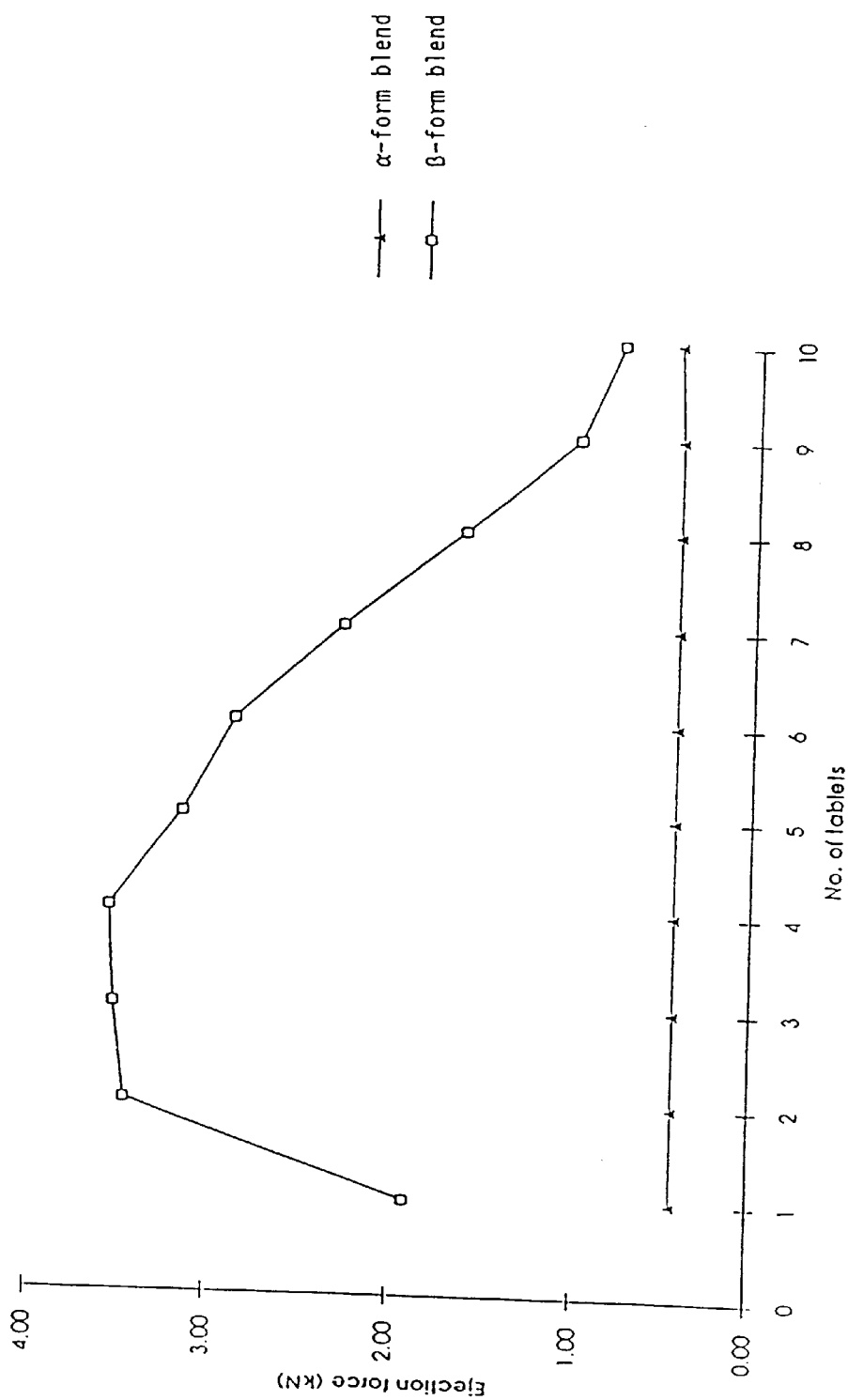

The measured ejection force for the last ten tablets of each blend is shown in FIG. 15. The tablets formed from the β-form required much greater force to remove them from the die. This effect manifested itself in the tablets being "flipped" from the die by the shoe.

The data obtained shows the poor processing properties of the β-form as compared to the α-form. The β-form has a low bulk density (fluff density=0.09 g ml$^{-1}$, compared with 0.36 g ml$^{-1}$ for the α-form) and poor flow properties and when blends containing it are tabletted, a large variability in tablet weight results and a high ejection force is required. In all these respects, the α-form has been shown to exhibit superior properties making it particularly suitable for pharmaceutical formulation.

(b) Hygroscopicity Study (i) The hygroscopicity of the α- and β-forms was assessed by gravimetric analysis as follows.

Samples of the α- and β-forms were separately placed in Kilner (trade mark) jars under the following conditions: 40° C.; 40° C. and 75%RH (relative humidity); and 40° C. and 95%RH. Water uptake of each sample was assessed gravimetrically, in triplicate, after selected time intervals.

Samples of the β-form stored at 40° C./75%RH or 40° C./95%RH for 1 day underwent a morphological change. Samples of the β-form stored at 40° C./95%RH for 1 day underwent a small weight loss (presumably after a weight increase due to water absorption followed by the morphological change and then moisture loss), whereas samples stored at 40° C./75%RH gained, on average, 6% of their original weight.

Figure 16:
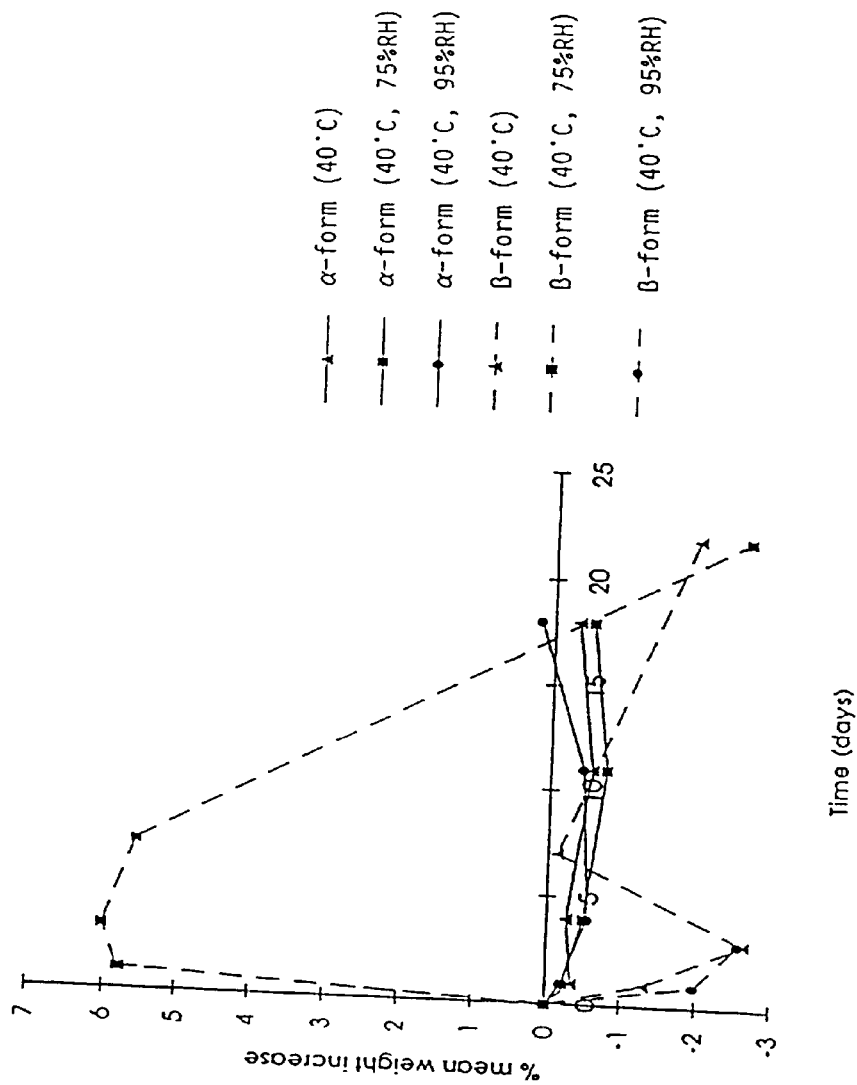
FIGS. 16–17 describe hygrscopicity data for certain polymorphs of (S,S,S)-N-(1-[2-carboxy-3-($N^2$-mesyllysylamino)propyl]-1-cyclopentylcarbonyl)tyrosine.

FIG. 16 shows the results obtained from the gravimetric analysis. The α-form was not found to be hygroscopic. However the β-form was found to be very hygroscopic at 40° C./75%RH.

(ii) Moisture microbalance experiments on the α- and β-forms confirmed that the α-form was not hygroscopic whereas the β-form was very hygroscopic.

Samples of the α- and β-forms were separately placed in the apparatus at 40° C. and allowed to equilibrate with the surroundings prior to the particular sample being exposed to increasing relative humidities, with equilibration periods between each increase in humidity.

Figure 17:
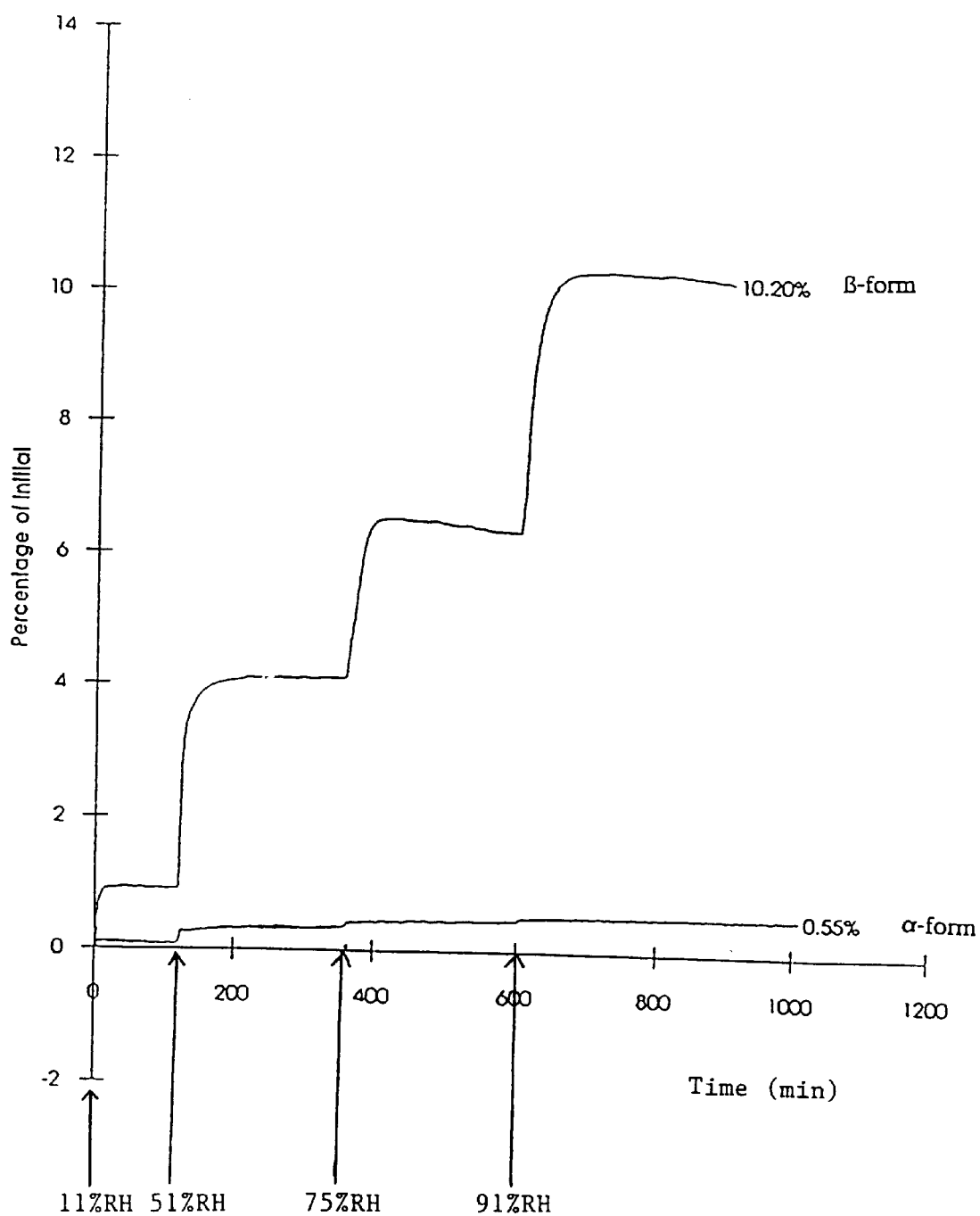

The results are shown in FIG. 17. These indicate that as much as 8% by weight of water (cf. original weight) was taken up by the β-form during the experiment.

The morphological change that the β-form underwent at high humidities was further studied and a transformation from a very low bulk density powder to a dense glassy solid was observed.

We claim:

1. A crystalline, α-polymorphic form of a compound of the formula:

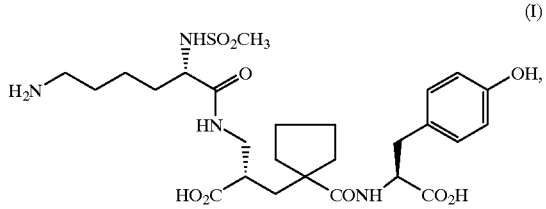

(I)

characterised by an infra-red spectrum as a mull in nujol which shows absorption bands at ν=3407, 3386, 3223, 3153, 1699, 1652, 1626, 1594, 1516, 1457 (nujol), 1377 (nujol), 1344, 1334, 1317, 1267, 1241, 1228, 1210, 1164, 1151, 1137, 1118, 1109, 1093, 1074, 1045, 1019, 1003, 981, 965, 911, 897, 862, 818, 800, 778, 762, 721 and 655 cm$^{-1}$.

2. A compound as claimed in claim 1 which is further characterised by a powder X-ray diffraction pattern obtained using copper radiation filtered with a graphite monochromator (λ=0.15405 nm) which shows main peaks at 7.5, 8.9, 9.9, 11.6, 15.6, 17.2, 17.5, 18.0, 20.2, 22.1 and 23.3 degrees 2θ.

3. A γ-polymorphic form of a compound of the formula (I) as defined in claim 1 characterised by an infra-red spectrum as a mull in nujol which shows absorption bands at ν=3377, 3240, 1665, 1639, 1594, 1527, 1518, 1494, 1457 (nujol), 1443, 1377 (nujol), 1344, 1321, 1304, 1254, 1195, 1178, 1162, 1143, 1111, 1098, 1046, 1031, 1012, 972, 962, 945, 932, 907, 879, 849, 815, 806, 780, 753, 729 and 658 cm$^{-1}$.

4. A compound as claimed in claim 3 which is further characterised by a powder X-ray diffraction pattern obtained using copper radiation filtered with a graphite monochromator (λ=0.15405 nm) which shows main peaks at 9.0, 9.6, 10.6, 11.6, 12.7, 13.3, 14.6, 16.2, 17.9, 18.8, 20.2 and 21.8 degrees 2θ.

5. A hydrated δ-form of a compound of the formula (I) as defined in claim 1 characterised by a water content of from 1 to 7% by weight, as determined by Karl Fischer analysis, and an infra-red spectrum as a mull in nujol which shows absorption bands at ν=3667, 3425, 3380, 3287, 3137, 3098, 1709, 1673, 1637, 1619, 1596, 1568, 1556, 1516, 1458 (nujol), 1448, 1419, 1390, 1378 (nujol), 1356, 1338, 1300, 1270, 1249, 1229, 1198, 1174, 1141, 1108, 1091, 1075, 1064, 1045, 1033, 1019, 1001, 985, 962, 941, 909, 889, 877, 841, 822, 807, 763, 744, 732, 721 and 655 cm$^{-1}$.

6. A compound as claimed in claim 5 which is further characterised by a powder X-ray diffraction pattern obtained using copper radiation filtered with a graphite monochromator (λ=0.15405 nm) which shows main peaks at 10.5, 10.8, 12.3, 14.5, 17.2, 17.6, 17.9, 18.9, 20.4, 21.5, 22.4, 23.0, 23.1, 24.7, 27.1, 27.8 and 28.9 degrees 2θ.

7. A compound as claimed in claim 6 which has a water content of from 2 to 4% by weight, as determined by Karl Fischer analysis.

8. A pharmaceutical composition comprising the α-polymorphic form of a compound of the formula (I) as claimed in claim 1 or 2, the γ-polymorphic form of a compound of the formula (I) as claimed in claim 3 or 4, or the hydrated δ-form of a compound of the formula (I) as claimed in claim 5, 6 or 7, together with a pharmaceutically acceptable diluent or carrier.

9. A composition as claimed in claim 8 wherein the α-polymorphic form of a compound of the formula (I) is present.

10. A method of treatment of an animal to treat a disease which is dependent on the inhibition of angiotensin converting enzyme and/or zinc dependent neutral endopeptidase E.C. 3.4.24.11 hypertension, congestive heart failure, renal insufficiency which comprises administering to said animal a said enzyme and/or said endopeptidase inhibitory amount of the α-polymorphic form of a compound of the formula (I) as claimed in claim 1 or 2, the γ-polymorphic form of a compound of the formula (I) as claimed in claim 3 or 4, or the hydrated δ-form of a compound of the formula (I) as claimed in claim 5, 6 or 7.

11. A method as claimed in claim 10 wherein the α-polymorphic form of a compound of the formula (I) or a composition thereof is used.

12. A sodium, potassium, ammonium or ($C_1$–$C_4$ alkyl) ammonium salt of a compound of the formula:

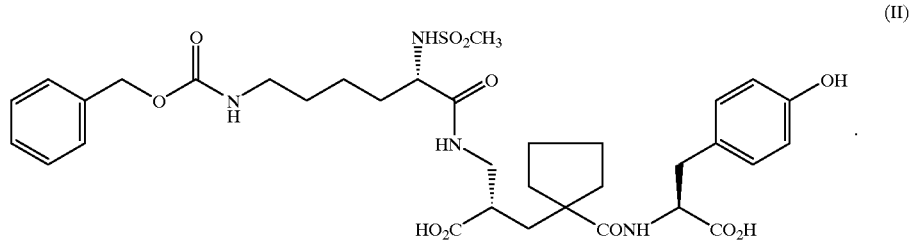

(II)

13. A sodium salt of a compound of the formula (II) as claimed in claim 12.

14. A compound of the formula:

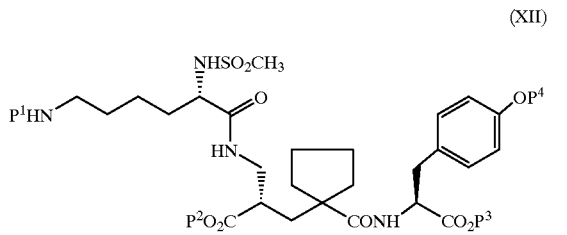

(XII)

wherein $P^1$, $P^2$, $P^3$ and $P^4$, which may be the same or different, are all protecting groups that are capable of removal, to provide a compound of the formula (I) as defined in claim 1, with the proviso that $P^1$ is not benzyloxycarbonyl when $P^2$, $P^3$ and $P^4$ are each t-butyl.

15. A compound as claimed in claim 14 wherein $P^1$ is formyl or benzyloxycarbonyl.

16. A compound as claimed in claim 14, wherein $P^2$, $P^3$ and $P^4$ are each t-butyl.

17. A compound of the formula:

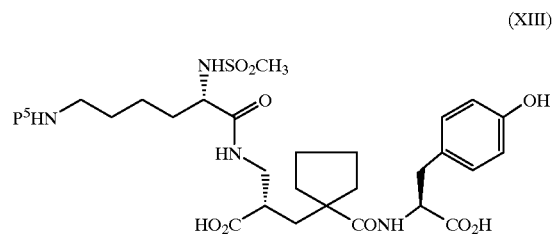

(XIII)

wherein $P^5$ is a protecting group that is capable of removal, to provide a compound of the formula (I) as defined in claim 1, with the proviso that $P^5$ is not benzyloxycarbonyl.

18. A compound as claimed in claim 17 wherein $P^5$ is formyl.

* * * * *